US009657048B2

(12) United States Patent
Schneller et al.

(10) Patent No.: US 9,657,048 B2
(45) Date of Patent: May 23, 2017

(54) ENANTIOMERS OF THE 1',6'-ISOMER OF NEPLANOCIN A

(71) Applicant: Auburn University, Auburn, AL (US)

(72) Inventors: Stewart W. Schneller, Auburn, AL (US); Chong Liu, Auburn, AL (US); Qi Chen, Auburn, AL (US); Wei Ye, Houston, TX (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 14/817,817

(22) Filed: Aug. 4, 2015

(65) Prior Publication Data

US 2016/0039860 A1    Feb. 11, 2016

Related U.S. Application Data

(60) Provisional application No. 62/032,926, filed on Aug. 4, 2014, provisional application No. 62/160,726, filed on May 13, 2015.

(51) Int. Cl.

| *A01N 43/90* | (2006.01) |
|---|---|
| *A61K 31/52* | (2006.01) |
| *A01N 43/42* | (2006.01) |
| *A61K 31/44* | (2006.01) |
| *C07D 473/00* | (2006.01) |
| *C07D 471/02* | (2006.01) |
| *C07D 491/02* | (2006.01) |
| *C07D 498/02* | (2006.01) |
| *C07H 19/16* | (2006.01) |
| *C07D 471/04* | (2006.01) |
| *C07D 473/30* | (2006.01) |
| *C07D 473/34* | (2006.01) |

(52) U.S. Cl.
CPC ........... *C07H 19/16* (2013.01); *C07D 471/04* (2013.01); *C07D 473/30* (2013.01); *C07D 473/34* (2013.01)

(58) Field of Classification Search
None
See application file for complete search history.

(56) References Cited

U.S. PATENT DOCUMENTS

| 4,138,562 | A | 2/1979 | Vince |
|---|---|---|---|
| 4,321,376 | A | 3/1982 | Otani et al. |
| 4,387,228 | A | 6/1983 | Montgomery et al. |
| 4,423,218 | A | 12/1983 | Otani et al. |
| 4,975,434 | A | 12/1990 | Marquez et al. |
| 5,629,454 | A | 5/1997 | Marquez et al. |
| 5,869,666 | A | 2/1999 | Marquez et al. |
| 7,341,983 | B2 | 3/2008 | Pedersen et al. |
| 8,211,869 | B2 | 7/2012 | Yu et al. |
| 8,629,275 | B2 | 1/2014 | Converso et al. |
| 2001/0036652 | A1 | 11/2001 | Yoshida et al. |
| 2003/0157697 | A1 | 8/2003 | Yoshida et al. |
| 2003/0162281 | A1 | 8/2003 | Yoshida et al. |
| 2003/0162282 | A1 | 8/2003 | Yoshida et al. |
| 2003/0175943 | A1 | 9/2003 | Yoshida et al. |
| 2007/0281883 | A1 | 12/2007 | Rosenfeld et al. |
| 2009/0270431 | A1 | 10/2009 | Chu et al. |
| 2011/0237606 | A1 | 9/2011 | Chai et al. |
| 2011/0269707 | A1 | 11/2011 | Stuyver et al. |

FOREIGN PATENT DOCUMENTS

| EP | 0383531 | A2 | 2/1990 |
|---|---|---|---|
| EP | 0477700 | A1 | 9/1991 |
| WO | 2006019105 | A1 | 8/2006 |
| WO | 2007047793 | | 4/2007 |

OTHER PUBLICATIONS

Yin, et. al.; Tetrahedron (2004), 60(15), 3451-3455.*
Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
International Search Report and Written Opinion, issued in connection to International Application No. PCT/US15/43617, 9 pages, Nov. 6, 2015.
Qi, Chen et. al., "Synthesis and antiviral activities of 3-deaza-2-fluoroaristeromycin and its 5' analogues", Bioorganic & Medicinal Chemistry 22 (2014), pp. 6961-6964.
National Center for Biotechnology Information, "Compound Summary for CID 66552950", U.S. National Library of medicine, http://pubchem.ncbi.nlm.nih.gov/compound/66552950, 10 pages, last accessed on Sep. 21, 2015.
National Center for Biotechnology Information, "Compound Summary for CID 71473514", U.S. National Library of medicine, http://pubchem.ncbi.nlm.nih.gov/compound/71473514, 9 pages, last accessed on Sep. 21, 2015.
Das, et. al., "5'-Nor carbocyclic 5'-deoxy-5'-(isobutylthio)adenosine and 2',3'-dideoxy-2', 3'-didehydro derivative", Antiviral Chemistry & Chemotherapy, vol. 12, pp. 119-124, 2001.
Wei, et. al. "The enantiomers of the 1', 6'-isomer of neplanocin A: Synthesis and antiviral properties", Bioorganic & Medicinal Chemistry 22 (2014) pp. 5315-5319.
Ludek, et. al., "New Convergent Synthesis of Carbocyclic Nucleoside Analogues", Synthesis (2003) vol. 13, pp. 2101-2109.
Herdewijin, Piet, "Modified Nucleosides in Biochemistry, Biotechnology and Medicine", WILEY-VCH Verlag GmbH & Co. KGaA, Weinheim (2008), 685 pages.

(Continued)

*Primary Examiner* — Jeffrey H Murray
(74) *Attorney, Agent, or Firm* — McKee, Voorhees & Sease, PLC

(57) ABSTRACT

Enantiomers of 1',6'-isoneplanocin, including derivatives of the enantiomers of 1',6'-isoneplanocin, are disclosed along with novel synthetic methods. In particular, a substituted cyclopentane epoxide is synthesized into the enantiomers of 1',6'-isoneplanocin. Enantiomers of carbocyclic nucleoside analogs of 3-deazaneplanocin to provide D- and L-like 1',6'-iso-3-deazaneplanocin are also disclosed. The small molecule chemotherapeutic compounds beneficially provide DNA and RNA antiviral activity, demonstrating activity towards, for example, human cytomegalovirus, measles, Ebola, norovirus, dengue, vaccinia and HBV. Compounds exhibiting reduced S-adenosylhomocysteine hydrolase inhibitory effects are disclosed and provide improved toxicity profiles in comparison to neplanocin. The invention provides improved prophylactic and/or therapeutic antiviral efficacy.

24 Claims, 7 Drawing Sheets

(56) References Cited

OTHER PUBLICATIONS

Kinoshita, et. al., "The Structure of Neplanocin C", Nucleosides and Nucleotides, (1985), vol. 4 (5), pp. 661-668.
Yin, et. al., "Isomers of neplanocin A and 2'-deoxyneplanocin A possessing a C-1' / C-6' double bond", Tetrahedron Letters, vol. 46, (2005), pp. 1927-1929.
Biggadike, et. al., "Use of Diethylaminosulphur Trifluoride (DAST) in the Preparation of Synthons of Carbocyclic Nucleosides", J. Chen. Soc. Perkin Trans vol. 1, (1998), pp. 549-554.
Siddiqi, et. al., "Antiviral Enantiomeric Perference for 5'-Noraristeromycin", Journal of Medicine Chemistry (1994), vol. 37, pp. 551-554.
Yang, et. al., "5'-Homoneplanocin A Inhibits Hepatitis B and Hepatitis C", Journal of Medicinial Chemistry, (2005), vol. 48, pp. 5043-5046.
Roy, et. al. "The 4',4'-difluoro analog of 5'-noraristeromycin: A new structural prototype for possible antiviral drug development toward orthopoxvirus and cytomegalovirus", Bioorganic & Medicinial Chemistry, vol. 13, (2005), pp. 4443-4449.
Ojwang, et. al., "Broad-spectrum inhibitor of viruses in the Flaviviridae family", Antiviral Research, vol. 68, (2005), pp. 49-55.
Julander, et. al., "Treatment of Venezuelan equine encephalitis virus infection with (—)-carbondine", Antiviral Research, vol. 80, (2008), pp. 309-315.
Gowen, et. al., "Efficacy of favipiravir (T-705) and T-1106 pyrazine derivatives in phlebovirus disease models", Antivial Research, vol. 86, (2010), pp. 121-127.
Roy, et. al., "3'-Fluoro-3'deoxy-5'-noraristeromycin derivatives: Synthesis and antiviral analysis", Bioorganic & Medicinial Chemistry, vol. 14, (2006) pp. 4980-4986.
Utah State University—Institute for Antiviral Research, "In Vitro Antiviral Testing", Utah State University, (2010), http://www.usu.edu/iar/htm/in-vitro-antiviral-testing, 4 pages; last accessed on Sep. 21, 2015.
Song, et. al., "Enantiomeric Synthesis of D- and L-Cyclopentenyk Nucleosides and Their Antiviral Activity Against HIV and West Nile Virus", Journal of Medicinal Chemistry, (2001), vol. 44, pp. 3985-3993.
Marce, et. al. "Synthesis of D- and L-Carbocyclic Nucleosides via Rhodium-Catalyzed Asymmetric Hydroacylation as the Key Step", Organic Letters vol. 10, No. 21 (2008), pp. 4735-4738.
Mahler, et. al., "Stereoselective Synthesis of D- and L-Carbocyclic Nucleosides by Enzymatically Catalyzed Kinetic Resolution", Chemical Eur J. (2012), vol. 18, pp. 11046-11062.
Wang, et. al., "Synthesis, Antiviral Activity, and Mechanism of Drug Resistance of D- and L-2', 3'-Didehydro-2', 3'-dideoxy-2'-fluorocarbocyclic Nucleosides", Journal of Medicinal Chemistry, vol. 48, (2005), pp. 3736-3748.
Seley, et. al., "Cabocyclic Isoadenosine Analogues of Neplanocin A", Organic Letters, (2003) vol. 5. No. 23, pp. 4401-4403.
Tosh, et al., "Syntheses and Biological Activity of Neplanocin and Analogues", Modified Nucleosides: in Biochemistry, Biotechnology and Medicine, 22, pages, Published 2008.
Kim, et al., "2-Substitution of N6-Benzyladenosine-5'-uronamides Enhances Selectivity for A3 Adenosine Receptors", J. Med. Chem., 8 pages, Published Sep. 1, 1994.

\* cited by examiner

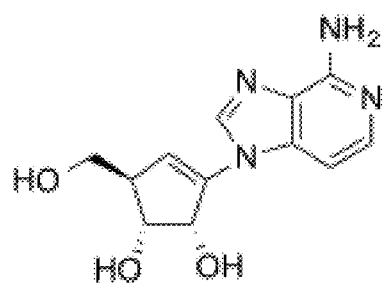 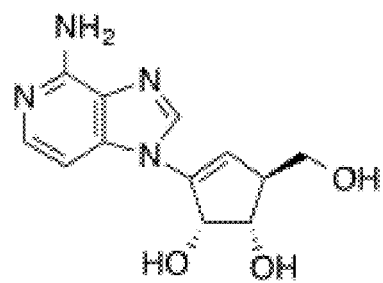
FIG. 8A                              FIG. 8B
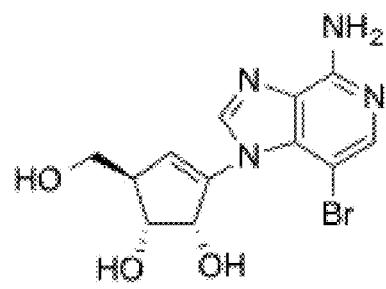 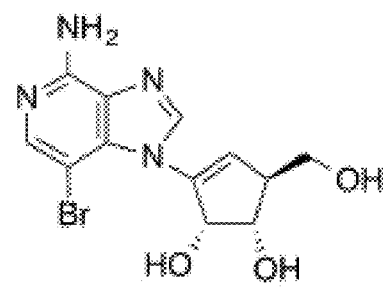
FIG. 8C                              FIG. 8D

ENANTIOMERS OF THE 1',6'-ISOMER OF NEPLANOCIN A

CROSS-REFERENCE TO RELATED APPLICATIONS

This application claims priority to U.S. Provisional Application Ser. Nos. 62/032,926 filed on Aug. 4, 2014 entitled Enantiomers of the 1',6'-Isomer of Neplanocin A: Synthesis and Antiviral Properties, and 62/160,726 filed on May 13, 2015 entitled 3-Deaza Enantiomers of the 1',6'-Isomer of Neplanocin A. The entire contents of these patent applications are hereby expressly incorporated herein by reference including, without limitation, the specification, claims, and abstract, as well as any figures, tables, or drawings thereof.

FIELD OF THE INVENTION

The invention relates to enantiomers of 1',6'-isoneplanocin, including derivatives of the enantiomers of 1',6'-isoneplanocin, provided by novel synthesis methods. In particular, a substituted cyclopentane epoxide is synthesized into the enantiomers of 1',6'-isoneplanocin. The invention further relates to carbocyclic nucleoside analogs of 3-deazaneplanocin to provide D- and L-like 1',6'-iso-3-deazaneplanocin. The small molecule chemotherapeutic compounds beneficially provide DNA and RNA antiviral activity, demonstrating activity towards, for example, human cytomegalovirus, measles, Ebola, norovirus, dengue, vaccinia and HBV. Compounds exhibiting reduced S-adenosylhomocysteine hydrolase inhibitory effects are disclosed and provide improved toxicity profiles in comparison to neplanocin. The invention provides improved prophylactic and/or therapeutic antiviral efficacy.

BACKGROUND OF THE INVENTION

A myriad of viral outbreaks have occurred throughout history, causing the deaths of hundreds of millions of people worldwide. Both DNA and RNA viruses are known and often transmitted by aerosols as well as by direct contact of contaminated surfaces. Viral infection may cause mild to severe symptoms in afflicted subjects, including humans. Accordingly, both prophylactic and therapeutic treatments remain a priority for development. However, both DNA and RNA viruses demonstrate rapid rate of mutation against therapeutic agents and as a result drug-resistant strains have become a concern for various viruses. New therapeutic agents are therefore needed to treat, cure and prevent viral infections.

Recent pandemic Ebola outbreaks in West Africa illustrate this need for treatment of viral hemorrhagic fevers (VHF), along with other viral infections. VHF are a collection of viral infections that are among the most feared human pathogens and thus an exemplary illustration for the need of broad spectrum antiviral compounds. VHF exist in four distinct families of RNA viruses: the Arenaviridae, Filoviridae, Bunyaviridae, and Flaviviridae. The Filoviridae Ebola is prominent among these pathogens but there are representatives within the other families that present ongoing threats (for example, dengue, a flavivirus). For Ebola there are four distinct species: Zaire ebolavirus (ZEBOV), Sudan ebolavirus (SEBOV), Ivory Coast ebolavirus (ICEBOV) (also known as Cote d'Ivoire ebolavirus (CIEBOV)), and Reston ebolavirus (REBOV). A new unnamed species of Ebola virus is suspected to be the causative agent of a recent outbreak of Ebola virus in Uganda. The highly contagious hemorrhagic fever virus originates from Africa and has a very high mortality rate. VHF viruses are transmitted by contact with bodily fluids from an infected subject and most often is fatal within a few days of hemorrhagic symptoms. These particular viruses attack endothelial cells of blood vessels, causing break down of blood vessels, allowing blood and serum to leak from the circulatory system.

Currently, there are no vaccines (except for yellow fever) or suitable drug candidates available to manage an uncontrollable outbreak and, as with the recent Ebola epidemic in West Africa only symptomatic measures are available for their treatment. As there are only a very limited number of possible therapeutics, for example, Ribavirin, a broad-spectrum antiviral agent with limited efficacy and extreme toxicity, few options are available for antiviral agents or vaccines for VHF. Because of limited access and the diversity of individual recipients' medical circumstances, vaccines pose issues that chemotherapeutic agents overcome. As a result, new therapeutic agents are needed to treat, cure, and prevent viral infections, including Ebola and other viral hemorrhagic fevers.

Naturally occurring neplanocin series of carbocyclic nucleosides or carbanucleosides are known as having the formulae shown in FIG. 1. The neplanocin compounds, namely neplanocin A, are known as having antiviral and antitumor activity as a result of the inhibition of S-adenosyl-L-homocysteine hydrolase (SAHase). SAHase catalyzes the interconversion of SAH into adenosine and L-homocysteine, and inhibition of this enzyme leads to an accumulation of SAH and a negative inhibition of cellular S-adenosyl-L-methionine (SAM)-dependent methyltransferase. Despite the potent enzyme inhibitory activity of neplanocin A, it has not been a clinically useful antiviral agent due to its potent toxicity to host cells. Another naturally-occurring carbocyclic nucleoside, aristeromycin, has been of interest due to its similar bioactivity. Various carbocyclic nucleosides have been synthesized as potential inhibitors of SAHase, although very few have been identified as potent inhibitors of SAHase, at least partly due to problems of the carbocycles to synthesize analogs to study. The carbocyclic nucleosides are thought to be synthetically a very challenging classification of nucleosides, requiring multiple, elaborate synthesis steps in order to introduce desired stereochemistry.

It has been identified that neplanocins offer a unique substitution pattern within the cyclopentenyl appendage. However the carbocyclic nucleosides are conformationally constrained by the alkene functionality or structural center. Changes to the C-1', C-6' isomer of neplanocin A disclosed pursuant to the present invention provide a framework for synthetic preparation of novel carbocyclic nucleosides in the neplanocin family of compounds. Accordingly, it is an objective of the claimed invention to develop enantiomers of 1',6'-isoneplanocin employing the alkene and epoxide structural centers to make molecular modifications resulting in improved biological activity of the neplanocins, particularly neplanocin A.

A further object of the invention is to provide a synthesis framework for the enantiomers of 1',6'-isoneplanocin.

A still further object of the invention is to provide methods of therapeutic or prophylactic antiviral treatment to complement vaccines, including employing the small molecule chemotherapeutic compounds disclosed herein. In particular, neplanocin derivatives are employed to treat or prevent DNA and/or RNA viruses, such as cytomegalovirus, measles, Ebola, norovirus, dengue, vaccinia or HBV. Preferably, compositions and methods of therapeutic or prophylactic antiviral treatment provide broad-spectrum antiviral activity.

Other objects, advantages and features of the present invention will become apparent from the following specification taken in conjunction with the accompanying drawings.

BRIEF SUMMARY OF THE INVENTION

In an embodiment, the present invention provides neplanocin derivatives having the following formulas:

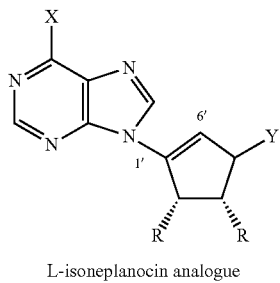

L-isoneplanocin analogue

Wherein R is a hydrogen or a hydroxyl group, halogen, or $C_1$-$C_4$ alkyl optionally substituted with a hydroxyl group, X is $NH_2$, NHR, NRR', NHOH, or hydrogen (wherein the R and R' in NHR and NRR' are alkyl, aryl or araalkyl), and Y is a hydrogen, a hydroxyl group, $CH_2OH$, $CH_2NH_2$ (NHR, NRR', (wherein the R and R' in NHR and NRR' are alkyl, aryl or araalkyl)), $CH_2X$ (wherein X is a halogen), or a $C_1$-$C_4$ alkyl optionally substituted with a hydroxyl group; or pharmaceutically-acceptable prodrug precursors and salts thereof.

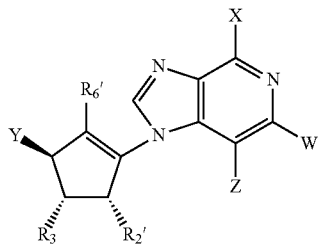

D-3-Deazaisoneplanocin analogue

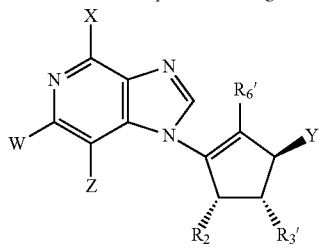

L-3-Deazaisoneplanocin analogue

Wherein R2' is a hydrogen or a hydroxyl group, halogen, or $C_1$-$C_4$ alkyl optionally substituted with a hydroxyl group, R3' is a hydrogen or a hydroxyl group, halogen, or $C_1$-$C_4$ alkyl optionally substituted with a hydroxyl group, R6' is a hydrogen or halogen (preferably F), W is a hydrogen or a halogen (preferably F), X is $NH_2$, NHR, NRR', NHOH, or hydrogen (wherein the R and R' in NHR and NRR' are alkyl, aryl or araalkyl), Y is a hydrogen, a hydroxyl group, $CH_2OH$, $CH_2NH_2$ (NHR, NRR', (wherein the R and R' in NHR and NRR' are alkyl, aryl or araalkyl)), $CH_2X$ (wherein X is a halogen), or a $C_1$-$C_4$ alkyl optionally substituted with a hydroxyl group, and Z is a hydrogen, halogen (preferably a F or Br), alkyl or substituted alkyl, cyano and derivatives therefrom; or pharmaceutically-acceptable prodrug precursors and salts thereof.

In an embodiment, the present invention provides methods of therapeutic or prophylactic treatment of a subject, including humans, against viral infection comprising: administering the disclosed neplanocin derivative(s) to a subject in need of antiviral therapeutic or prophylactic treatment. In an aspect, the virus is a DNA virus or an RNA virus. In a preferred aspect, the virus in a negative strand RNA virus.

In an embodiment, the present invention provides pharmaceutical compositions for treating a subject, including a human, with a viral infection or in need of prophylactic antiviral treatment comprising: a sufficient amount of the neplanocin derivative(s) to produce antiviral effects.

In an aspect, the pharmaceutical composition further comprises a pharmaceutically acceptable carrier. In an aspect, the pharmaceutical composition further comprises a pharmaceutically acceptable excipient. In an aspect, the antiviral amount of the neplanocin derivative is an amount sufficient to improve, inhibit, prevent or ameliorate the viral infection.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 8A-D show neplanocin analogues evaluated according to embodiments of the invention: D-3-deazaisoneplanocin (FIG. 8A), L-3-deazaisoneplanocin (FIG. 8B), D-3-bromo-3-deazaneplanocin (FIG. 8C) and L-3-bromo-3-deazaneplanocin (FIG. 8D).

Figure 1A:
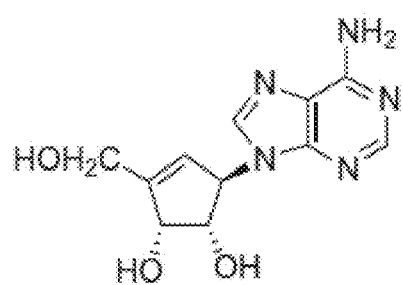
FIGS. 1A-1E show the naturally-occurring neplanocins, including Neplanocin A (FIG. 1A), Neplanocin B (FIG. 1B), Neplanocin C (FIG. 1C), Neplanocin D (FIG. 1D), Neplanocin F (FIG. 1E).
Figure 1B:
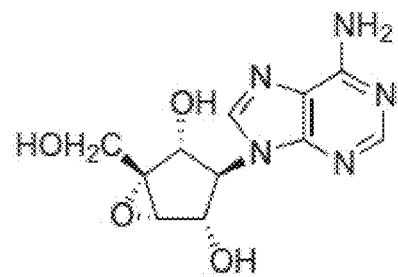
Figure 1C:
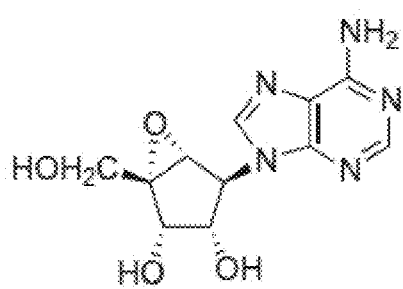
Figure 1D:
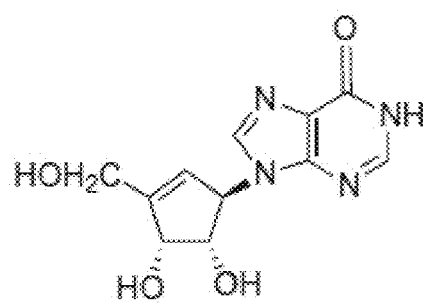
Figure 1E:
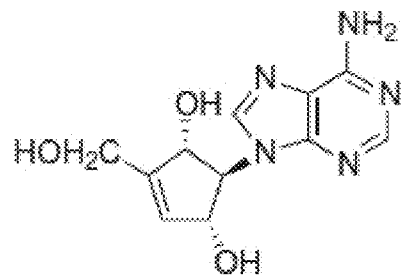

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates to enantiomers of 1',6'-isoneplanocin, including derivatives of the enantiomers of 1',6'-isoneplanocin, provided by novel synthesis methods. The compounds provide advantages over existing, naturally-occurring neplanocin compounds in antiviral assays and/or reduced toxicity and/or adverse effects. For example, the enantiomers of 1',6'-isoneplanocin demonstrate activity towards human cytomegalovirus, measles, Ebola, norovirus, dengue, vaccinia and HBV. Moreover, various enantiomers of 1',6'-isoneplanocin exhibit reduced S-adenosylhomocysteine hydrolase (SAHase) inhibitory effects thereby providing improved toxicity profiles in comparison to neplanocin, as prolonged inhibition of SAHase overtakes cellular protein synthesis and leads to severe toxicity. Beneficially, as disclosed pursuant to the present invention, antiviral neplanocin derivatives may provide decreased SAHase inhibition allowing cellular mRNA cap methylation and full protein synthesis and thereby providing antiviral efficacy without general toxicity.

The embodiments of this invention are not limited to particular compounds, methods of preparation and/or treatment, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups. In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "substituted" as referred to herein refers to a substitution at a carbon (or nitrogen) position mentioned, with the referenced group, which may include herein hydroxyl, carboxyl, cyano, nitro, halogen(s), thiol, alkyl group (preferably $C_1$-$C_6$), alkoxyl group (preferably $C_1$-$C_6$ alkyl or arly, including phenyl), ester, including alkylene esters, thioether, thioester, nitro or amines, alkanol, alkanoic acids or the like.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The compounds, compositions, and methods of the present invention may comprise, consist essentially of, or consist of the components and steps disclosed herein as well as other components and steps described herein. As used herein, "consisting essentially of" means that the compounds, compositions, and methods may include additional components and steps, but only if the same do not materially alter the basic and novel characteristics of the claimed compounds, compositions, and methods.

Methods of Synthesis

According to an embodiment of the invention methods of synthesizing neplanocin series of carbocyclic nucleosides are provided, namely neplanocin analogues having a C1'=C6'. In an embodiment, methods of synthesizing neplanocin analogues are provided, including enantiomers of 1',6'-isoneplanocin and neplanocin derivatives.

Figure 2:
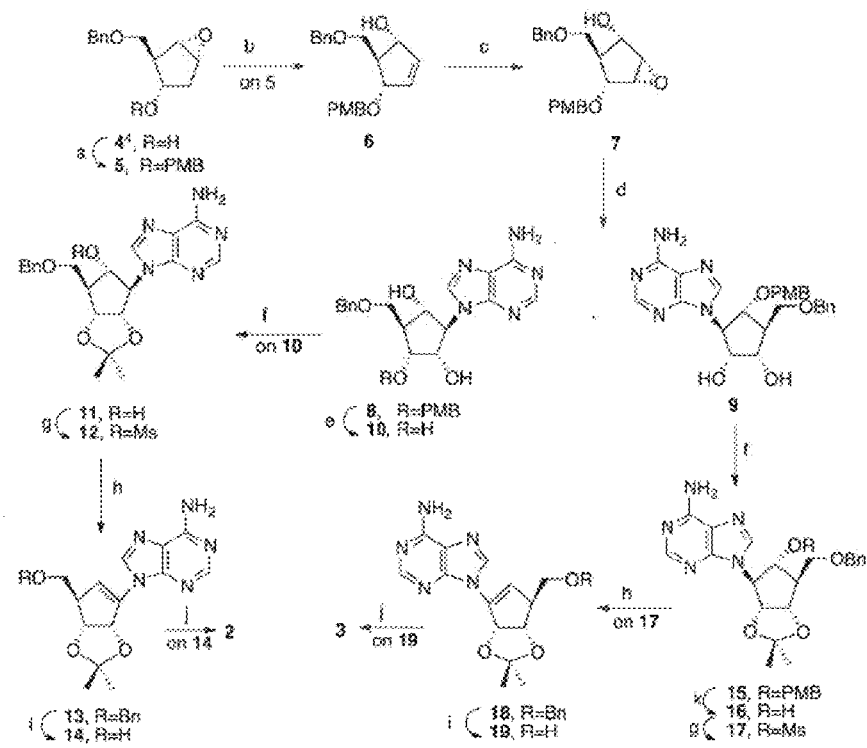
FIG. 2 shows a schematic of the synthesis methods according to an embodiment of the invention to synthesize the neplanocin analogues D-like isoneplanocin and L-like isoneplanocin employing the following reagents and conditions: (a) NaH, PMBBr, TBAI, THF, 95%; (b) LiHMDS, THF, 84%; (c) mCPBA, $CH_2Cl_2$, 84%; (d) adenine, DBU, DMF, 50% for 8, 31% for 9; (e) 1 N HCl/MeOH, 94%; (f) p-TsOH—$H_2O$, CH(OEt)$_3$, acetone, 77% for 11, 84% for 15; (g) MsCl, Et$_3$N, $CH_2Cl_2$, 93% for 12, 90% for 17; (h) NaOMe, THF/MeOH, 89% for 13, 90% for 18; (i) Pd(OH)$_2$/C, cyclohexene, EtOH, 87% for 14, 87% for 19; (j) 2 N HCl/MeOH, 90% for 2, 92% for 3; (k) DDQ, $CH_2Cl_2$/$H_2O$, 93%.
Figures 3A, 3B:
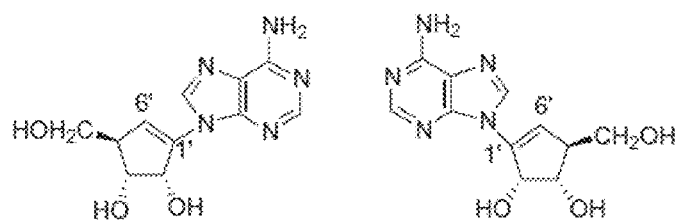
FIGS. 3A and 3B show neplanocin analogues D-like isoneplanocin (FIG. 3A) and L-like isoneplanocin (FIG. 3B) synthesized according to an embodiment of the invention.

FIG. 2 shows a schematic of the synthesis steps for generating neplanocin analogues. The depicted non-limiting embodiment of the invention outlines synthesis steps, reagents and conditions for the target neplanocin analogues enantiomers, D-like isoneplanocin and L-like isoneplanocin (formulas shown in FIG. 3A-B, respectively).

As depicted, in an embodiment the methods employ a substituted cyclopentyl epoxide 4 (available from cyclopentadiene in two steps) to initiate the synthesis reaction with protection of the secondary hydroxyl of 4 with ap-methoxybenzyl (PMB) group to 5. (See Ludek & Meier, Synthesis 2003, 13, 2101; Biggadkike et al., J. Chem. Soc., Perkin Trans, 1 1998, 549) The cyclopentenol can be enantioselectively prepared from alkylated cyclopentadiene in several steps. A regioselective ring opening of 5 with lithium bis(trimethylsilyl) amide (LiHMDS) provided the versatile alkene 6. Subsequent oxidation of 6 with m-chloroperoxybenzoic acid (mCPBA) proceeded to the epoxide 7 providing an entry point to the carbocyclic nucleoside scaffold. The expoxide 7 is reacted with adenine in the presence of 1,8-diazabicycloundec-7-ene (DBU) to produce a mixture of 8 and 9 (1.6:1). Thereafter, acidic removal of the PMB group of 8 to 10 is then followed by glycol protection to produce 11. Mesylation of 11 produces 12, which undergoes elimination in the presence of sodium methoxide to produce 13. Debenzylation of 13 with subsequent deketalization produces the D-like isoneplanocin 2 (depicted as FIG. 3A).

As further depicted in FIG. 2, in an embodiment the methods employ a substituted cyclopentyl epoxide 4 (available from cyclopentadiene in two steps) to initiate the synthesis reaction with protection of the secondary hydroxyl of 4 with a p-methoxybenzyl (PMB) group to 5. (See Ludek & Meier, Synthesis 2003, 13, 2101; Biggadkike et al., J. Chem. Soc., Perkin Trans, 1 1998, 549) A regioselective ring opening of 5 with lithium bis(trimethylsilyl) amide (LiHMDS) provided the versatile alkene 6. Subsequent oxidation of 6 with m-chloroperoxybenzoic acid (mCPBA) proceeded to the epoxide 7 providing an entry point to the carbocyclic nucleoside scaffold. The epoxide 7 is reacted with adenine in the presence of 1,8-diazabicycloundec-7-ene (DBU) to produce a mixture of 8 and 9 (1.6:1). The glycol protection of 9 to 15 is the synthesis step which diverts the methods towards the production of the L-like isoneplanocin 3 (depicted as FIG. 3B). Oxidative deprotection with 2,3-dichloro-5,6-dicyano-1,4-benzoquinone (DDQ) converts 15 into 16. As with 11, mesylation of 16 to 17 and subsequent sodium methoxide promote elimination and produce 18 (which is analogous to 13 in the synthesis of the D-like analogue). Deprotection of 18 (elimination in the presence of sodium methoxide) produces 19 and then 1 N hydrochloric acid removes the isopropylene group to produce the L-like isoneplanocin 3.

In an embodiment the synthesis methods set forth herein provide a method for generating neplanocin A analogues as disclosed herein. Additional neplanocin A analogues can be synthesized by these methods.

Analogue Compounds—Neplanocin Derivatives

In an aspect of the invention, analogues of 1,6-isomers of neplanocin A as disclosed as beneficial targets for medicinal chemists and organic chemists due to their novel analogue structures and unexpected biological activity.

According to an embodiment of the invention a neplanocin derivative having the following formula ("L"-like isoneplanocin analogue, Structure I) is provided:

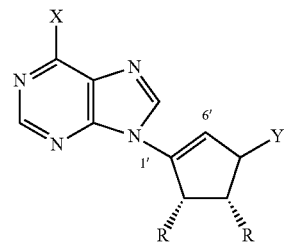

Wherein R is a hydrogen or a hydroxyl group, halogen, or $C_1$-$C_4$ alkyl optionally substituted with a hydroxyl group (or combination of the same such that R is the same or is different), wherein Y is a hydrogen, a hydroxyl group, $CH_2OH$, $CH_2NH_2$ (NHR, NRR', wherein the R and R' in NHR and NRR' are alkyl, aryl or araalkyl), $CH_2X$ (wherein X is a halogen), or a $C_1$-$C_4$ alkyl optionally substituted with a hydroxyl group, and wherein X is $NH_2$, NHR, NRR', NHOH, or hydrogen (wherein the R and R' in NHR and NRR' are alkyl, aryl or araalkyl); or pharmaceutically-acceptable prodrug precursors and salts thereof.

In a preferred aspect, the "L"-like isoneplanocin analogue has a structure wherein R is a hydrogen or a hydroxyl group, wherein Y is a hydrogen, a hydroxyl group, or $CH_2OH$, and wherein X is $NH_2$ or hydrogen; or pharmaceutically-acceptable prodrug precursors and salts thereof.

In a preferred aspect, the "L"-like isoneplanocin analogue has the following structure:

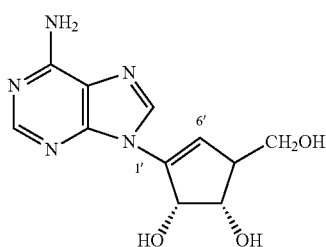 [SMILES: Nc1ncnc2c1ncn2C1=CC(CO)[C@H](O)[C@@H]1O]

According to an embodiment of the invention a neplanocin derivative having the following formula ("D"-like isoneplanocin analogue, Structure II) is provided:

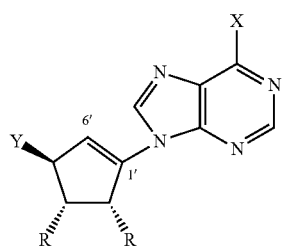

Wherein R is a hydrogen or a hydroxyl group, halogen, or $C_1$-$C_4$ alkyl optionally substituted with a hydroxyl group (or combination of the same such that R is the same or is different), wherein Y is a hydrogen, a hydroxyl group, $CH_2OH$, $CH_2NH_2$ (NHR, NRR', wherein the R and R' in NHR and NRR' are alkyl, aryl or araalkyl), $CH_2X$ (wherein X is a halogen), or a $C_1$-$C_4$ alkyl optionally substituted with a hydroxyl group, and wherein X is $NH_2$, NHR, NRR', NHOH, or hydrogen (wherein the R and R' in NHR and NRR' are alkyl, aryl or araalkyl); or pharmaceutically-acceptable prodrug precursors and salts thereof.

In a preferred aspect, the "D"-like isoneplanocin analogue has a structure wherein R is a hydrogen or a hydroxyl group, wherein Y is a hydrogen, a hydroxyl group, or $CH_2OH$, and wherein X is $NH_2$ or hydrogen; or pharmaceutically-acceptable prodrug precursors and salts thereof.

According to an embodiment of the invention a neplanocin derivative having the following formula ("D"-like 3-Deazaisoneplanocin analogue (or D-1',6'-iso-3-deazaneplanocin), Structure III) is provided:

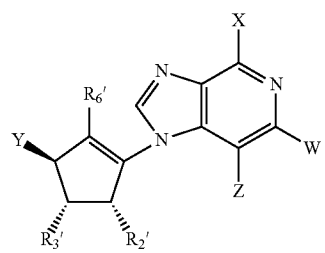

Wherein R2' is a hydrogen or a hydroxyl group, halogen, or $C_1$-$C_4$ alkyl optionally substituted with a hydroxyl group, wherein R3' is a hydrogen or a hydroxyl group, halogen, or $C_1$-$C_4$ alkyl optionally substituted with a hydroxyl group, wherein R6' is a hydrogen or halogen (preferably F), wherein W is a hydrogen or a halogen (preferably F), wherein X is $NH_2$, NHR, NRR', NHOH, or hydrogen (wherein the R and R' in NHR and NRR' are alkyl, aryl or araalkyl), wherein Y is a hydrogen, a hydroxyl group, $CH_2OH$, $CH_2NH_2$ (NHR, NRR', wherein the R and R' in NHR and NRR' are alkyl, aryl or araalkyl), $CH_2X$ (wherein X is a halogen), or a $C_1$-$C_4$ alkyl optionally substituted with a hydroxyl group, and wherein Z is a hydrogen, halogen, alkyl or substituted alkyl, cyano and derivatives therefrom; or pharmaceutically-acceptable prodrug precursors and salts thereof.

In a preferred aspect, the "D"-like 3-Deazaisoneplanocin analogue has a structure wherein R2' and/or R3' and/or R6' are a hydrogen or a hydroxyl group, wherein W is a hydrogen or a halogen, wherein X is $NH_2$ or hydrogen, wherein Y is hydrogen, hydroxyl group, or $CH_2OH$, and wherein Z is a halogen, preferably F, Cl, Br or I, more preferably F or Br, preferably Br; or pharmaceutically-acceptable prodrug precursors and salts thereof.

In a preferred aspect, the "D"-like 3-Deazaisoneplanocin analogue has the following structure:

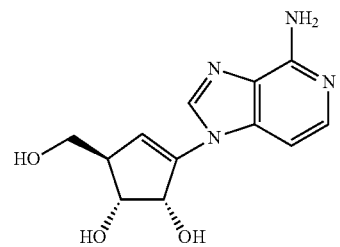 [SMILES: Nc1nccc2c1ncn2C1=C[C@H](CO)[C@@H](O)[C@H]1O]

According to an embodiment of the invention a neplanocin derivative having the following formula ("D"-like 3-halo-3-Deazaisoneplanocin analogue) is provided:

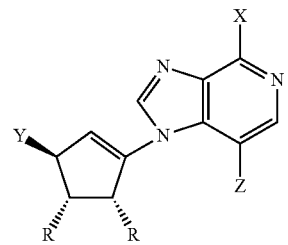

Wherein R is a hydrogen or a hydroxyl group, halogen, or $C_1$-$C_4$ alkyl optionally substituted with a hydroxyl group (or combination of the same such that R is the same or is different), wherein Y is a hydrogen, a hydroxyl group, $CH_2OH$, $CH_2NH_2$ (NHR, NRR', wherein the R and R' in NHR and NRR' are alkyl, aryl or araalkyl), $CH_2X$ (wherein X is a halogen), or a $C_1$-$C_4$ alkyl optionally substituted with a hydroxyl group, and wherein X is $NH_2$, NHR, NRR', NHOH, or hydrogen (wherein the R and R' in NHR and NRR' are alkyl, aryl or araalkyl), and wherein Z is a halogen, preferably F, Cl, Br or I, more preferably F or Br, preferably Br; or pharmaceutically-acceptable prodrug precursors and salts thereof.

In a preferred aspect, the analogue is a "D"-like 3-bromo-3-Deazaisoneplanocin (or 3-bromo-1',6'-iso-3-deazaneplanocin) having the following structure:

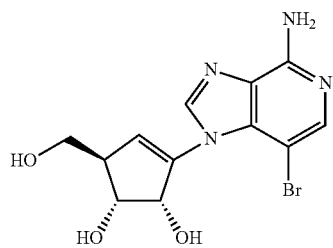 [SMILES: Nc1ncc(Br)c2c1ncn2C1=C[C@H](CO)[C@@H](O)[C@H]1O]

According to an embodiment of the invention a neplanocin derivative having the following formula ("L"-like 3-Deazaisoneplanocin analogue (or L-1',6'-iso-3-deazaneplanocin), Structure IV) is provided:

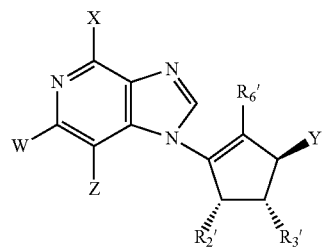

Wherein R2' is a hydrogen or a hydroxyl group, halogen, or $C_1$-$C_4$ alkyl optionally substituted with a hydroxyl group, wherein R3' is a hydrogen or a hydroxyl group, halogen, or $C_1$-$C_4$ alkyl optionally substituted with a hydroxyl group, wherein R6' is a hydrogen or halogen (preferably F), wherein W is a hydrogen or a halogen (preferably F), wherein X is $NH_2$, NHR, NRR', NHOH, or hydrogen (wherein the R and R' in NHR and NRR' are alkyl, aryl or araalkyl), wherein Y is a hydrogen, a hydroxyl group, $CH_2OH$, $CH_2NH_2$ (NHR, NRR', wherein the R and R' in NHR and NRR' are alkyl, aryl or araalkyl), $CH_2X$ (wherein X is a halogen), or a $C_1$-$C_4$ alkyl optionally substituted with a hydroxyl group, and wherein Z is a hydrogen, halogen, alkyl or substituted alkyl, cyano and derivatives therefrom; or pharmaceutically-acceptable prodrug precursors and salts thereof.

In a preferred aspect, the "L"-like 3-Deazaisoneplanocin analogue has the following structure:

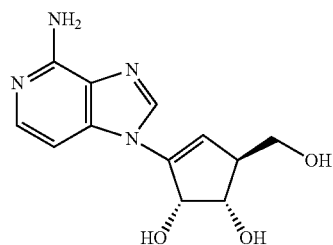 [SMILES: Nc1nccc2c1ncn2C1=C[C@@H](CO)[C@H](O)[C@@H]1O]

According to an embodiment of the invention a neplanocin derivative having the following formula ("L"-like 3-halo-3-Deazaisoneplanocin analogue) is provided:

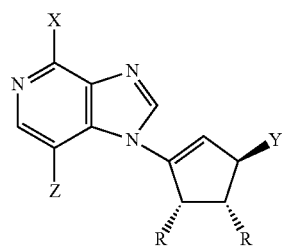

Wherein R is a hydrogen or a hydroxyl group, halogen, or $C_1$-$C_4$ alkyl optionally substituted with a hydroxyl group (or combination of the same such that R is the same or is different), wherein Y is a hydrogen, a hydroxyl group, $CH_2OH$, $CH_2NH_2$ (NHR, NRR', wherein the R and R' in NHR and NRR' are alkyl, aryl or araalkyl), $CH_2X$ (wherein X is a halogen), or a $C_1$-$C_4$ alkyl optionally substituted with a hydroxyl group, and wherein X is $NH_2$, NHR, NRR', NHOH, or hydrogen (wherein the R and R' in NHR and NRR' are alkyl, aryl or araalkyl), and wherein Z is a halogen, preferably F, Cl, Br or I, more preferably F or Br, preferably Br; or pharmaceutically-acceptable prodrug precursors and salts thereof.

In a preferred aspect, the analogue is a "L"-like 3-bromo-3-Deazaisoneplanocin (or 3-bromo-1',6'-iso-3-deazaneplanocin) having the following structure:

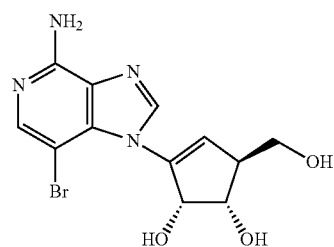 [SMILES: Nc1ncc(Br)c2c1ncn2C1=C[C@@H](CO)[C@H](O)[C@@H]1O]

According to a further embodiment of the invention a neplanocin derivative having the following formula ("L"-like isoneplanocin analogue) is provided:

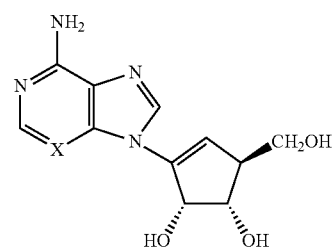

Wherein X is N (isoneplanocin), CH (iso-3-deazaneplanocin), or C(halogen), such as CBr (iso-3-bromo-deazaneplanocin); or pharmaceutically-acceptable prodrug precursors and salts thereof.

According to a further embodiment of the invention a neplanocin derivative having the following formula ("D"-like neplanocin analogue) is provided:

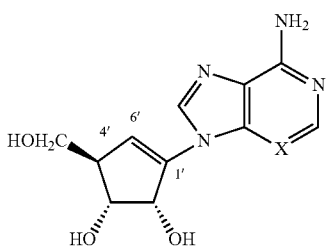

Wherein X is N (isoneplanocin), CH (iso-3-deazaneplanocin), or C(halogen), such as CBr (iso-3-bromo-deazaneplanocin); or pharmaceutically-acceptable prodrug precursors and salts thereof.

In still further embodiments, neplanocin derivatives which are D-like analogues are modified for SAHase focused antiviral efficacy, as shown in the following formula:

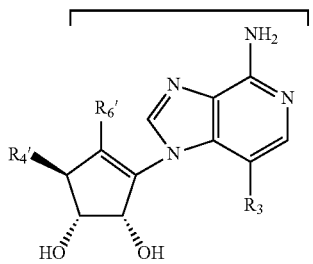

Wherein R4' is $CH_2F$, hydroxyl, or hydrogen, and wherein R6' is a hydrogen or a halogen, such as Fluorine, and wherein R3 is a hydrogen, hydroxyl or a halogen, such as bromine. In some aspects the R3 retains the R3' OH for the SAHase inhibitory activity by the generally accepted cofactor depletion mechanism but does not contain the R4' center of the L-series neplanocin derivatives and thereby eliminates susceptibility to, for example, nucleotide formation. As a result these D-like analogues provide enhancing SAHase inhibition.

In still further embodiments, neplanocin derivatives which are L-like analogues with R4' target likely have a kinase role in antiviral activity, as shown in the following formula:

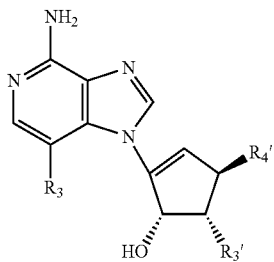

Wherein R3 is hydrogen or a halogen, such as fluorine or bromine, and wherein R4' is a $CH_2OH$, $CH(Me)OH$, or $CH_2CH_2OH$. In an aspect, the L-like compounds target the R4' $CH_2OH$ center where a kinase may be playing an antiviral mechanism of action. Without being limited to a particular mechanism of action, the elimination of the R3' OH for SAHase inhibition (by removing the hydroxyl or replacing it with the bioisoteric halogen, such as fluorine) to avoid any complication that could arise by SAHase inhibition. Further neplanocin derivatives include the R4' side chains presenting steric interference at the hydroxyl center (e.g. R4' as CH(Me)OH) and hydroxyl relocation with R4' as $CH_2CH_2OH$.

In still further embodiments, neplanocin derivatives which are D or L-like (not shown) analogues that do not result in SAHase inhibition nor R4' $CH_2OH$ as previously described may be synthesized to have the following formula:

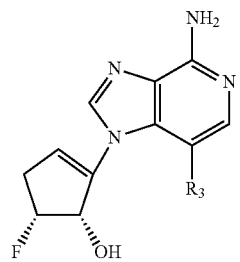

Wherein R3 is a hydrogen or a halogen, such as bromine.

According to still further embodiments of the invention a neplanocin derivative having the following formulae are provided:

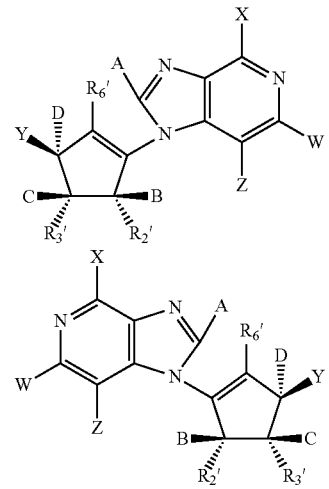

Wherein R2' is a hydrogen or a hydroxyl group, halogen, or $C_1$-$C_4$ alkyl optionally substituted with a hydroxyl group, wherein R3' is a hydrogen or a hydroxyl group, halogen, or $C_1$-$C_4$ alkyl optionally substituted with a hydroxyl group, wherein R6' is a hydrogen or halogen (preferably F), wherein A is alkyl, alkylX (wherein X is halo, hydroxy, or cyano), aryl, vinyl, wherein B is alkyl, hydroxy or halo, wherein C is alkyl, hydroxy or halo, wherein D is alkyl, alkylX (wherein X is halo, hydroxy, or cyano), or vinyl, wherein W is a hydrogen or a halogen (preferably F), wherein X is $NH_2$, NHR, NRR', NHOH, or hydrogen (wherein the R and R' in NHR and NRR' are alkyl, aryl or araalkyl), wherein Y is a hydrogen, a hydroxyl group, $CH_2OH$, $CH_2NH_2$ (NHR, NRR', wherein the R and R' in NHR and NRR' are alkyl, aryl or araalkyl), $CH_2X$ (wherein X is a halogen), or a $C_1$-$C_4$ alkyl optionally substituted with a hydroxyl group, and wherein Z is a hydrogen, halogen, alkyl or substituted alkyl, cyano and derivatives therefrom; or pharmaceutically-acceptable prodrug precursors and salts thereof.

As referred to herein, the designations D-like and L-like refer to the enantiomeric structures of the neplanocin derivatives. The designations D-like and L-like carbocyclic nucleosides are used herein to draw analogy to the natural D-, and their enantiomeric L-, ribofuranosyl nucleosides.

As referred to herein, halogens include the group 17 elements: fluorine (F), chlorine (Cl), bromine (Br), iodine (I), and astatine (At). Halogens may further include artificially created elements.

As referred to herein, if a moiety is described as being "optionally substituted", the moiety may be either substituted or unsubstituted.

Unless otherwise indicated, any reference to the neplanocin derivative compounds herein by structure, formula, name or any other means, includes pharmaceutically acceptable salts, such as sodium, potassium, and ammonium salts; alternate solid forms, such as polymorphs, solvates, hydrates, etc.; tautomers; or, any other chemical species that may rapidly convert to a compound described herein under conditions in which the compounds are used as described herein.

In an embodiment, the neplanocin derivatives may further include the product precursors thereof. The term "prodrug" refers to derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner by reaction of a functional group of the compound (such as an amino, hydroxy or carboxy group). Prodrugs often offer advantages of solubility, tissue compatibility, or delayed release in mammals, such as described in Bungard, H., Design Of Prodrugs, pp. 7-9, 21-24, Elsevier, Amsterdam 1985, which is herein incorporated by reference in its entirety.

Pharmaceutical Compositions

According to an embodiment of the invention a pharmaceutical composition for treating a subject with a viral infection or in need of prophylactic antiviral treatment is provided. A composition according to the invention includes an antiviral effective amount or a therapeutically-effective amount of at least one of the neplanocin derivatives (analogue compounds) disclosed herein.

As one skilled in the art will ascertain, an antiviral effective amount or an amount sufficient to treat (e.g. therapeutically effective amount) refers to the amount of a pharmaceutical composition administered to improve, inhibit, or ameliorate a condition of a subject, or a symptom of a disorder, in a clinically relevant manner (e.g., improve, inhibit, or ameliorate infection by a virus, such as the Ebola virus, or one or more symptoms that occur following infection by the virus). Any improvement in the subject is considered sufficient to achieve treatment. Preferably, an amount sufficient to treat is an amount that prevents the occurrence or one or more symptoms of the infection or is an amount that reduces the severity of, or the length of time during which a subject suffers from, one or more symptoms of the infection (e.g., by at least 10%, 20%, or 30%, more preferably by at least 50%, 60%, or 70%, and most preferably by at least 80%, 90%, 95%, 99%, or more, relative to a control subject that is not treated with a composition of the invention).

Moreover, one skilled in the art will ascertain, an antiviral effective amount or an amount sufficient to treat may also refer to the amount of a pharmaceutical composition containing at least one of the neplanocin derivatives administered to reduce or kill virus cells (e.g., by at least 50%, 60%, or 70%, and most preferably by at least 80%, 90%, 95%, 99%, or 100%).

A sufficient amount of the pharmaceutical composition containing at least one of the neplanocin derivatives used to practice the methods described herein (e.g., the treatment or prophylaxis of viral infection) varies depending upon the nature of the particular virus and infection which can be determined by standard clinical techniques, route of administration and the age, body weight, and general health of the subject being treated. Ultimately, the prescribers or researchers will decide the appropriate amount and dosage. In some aspects, in vitro assays are optionally employed to help identify optimal dosage ranges. The precise dose to be employed should be decided according to the judgment of the practitioner and each subject's circumstances. However, suitable dosage ranges for intravenous administration are generally about 20 to 500 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems. Suppositories generally contain active ingredient in the range of 0.5% to 10% by weight; oral formulations preferably contain 10% to 95% active ingredient.

By "pharmaceutical composition" the neplanocin derivative(s) of the present invention provide the therapeutically or biologically active agent for formulation into a suitable delivery means for administration to a subject. For the purposes of this invention, pharmaceutical compositions suitable for delivering the neplanocin derivatives can include, e.g., tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of the aforementioned formulations can be prepared by well-known and accepted methods of art. See, for example, Remington: The Science and Practice of Pharmacy (21st edition), ed. A. R. Gennaro, Lippincott Williams & Wilkins, 2005, and Encyclopedia of Pharmaceutical Technology, ed. J. Swarbrick, Informa Healthcare, 2006, each of which is hereby incorporated by reference.

In an aspect, the pharmaceutical compositions comprise at least one of the neplanocin derivatives and a pharmaceutically acceptable carrier or excipient. The term "pharmaceutically acceptable" means approved by a regulatory agency of the Federal or a state government or listed in the U.S. Pharmacopeia or other generally recognized pharmacopeia for use in animals, and more particularly in humans.

Examples of suitable pharmaceutically acceptable carriers or excipients that can be used in said pharmaceutical compositions include, but are not limited to, sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, phosphate buffer solutions, lubricants, coloring agents, releasing agents, coating agents, sweetening, flavoring or perfuming agents, preservatives, or antioxidants.

The term "excipient" refers to additives and stabilizers typically employed in the art (all of which are termed "excipients"), including for example, buffering agents, stabilizing agents, preservatives, isotonifiers, non-ionic detergents, antioxidants and/or other miscellaneous additives. Stabilizers refer to a broad category of excipients which can range in function from a bulking agent to an additive which solubilizes the neplanocin derivative or helps to prevent denaturation of the same. Additional conventional excipients include, for example, fillers (e.g., starch), chelating agents (e.g., EDTA), antioxidants (e.g., ascorbic acid, methionine, vitamin E) and cosolvents.

The term "carrier" refers to a diluent, adjuvant, excipient, or vehicle with which the pharmaceutical composition is administered. Such pharmaceutical carriers are illustratively sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions are optionally employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, also contains wetting or emulsifying agents, or pH buffering agents. These compositions optionally take the form of solutions, suspensions, emulsion, tablets, pills, capsules, powders, sustained release formulations and the like. The composition is optionally formulated as a suppository, with traditional binders and carriers such as triglycerides. Oral formulation illustratively includes standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, which is herein incorporated by reference in its entirety.

In an aspect, pharmaceutical compositions according to the invention may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain a therapeutic level. One skilled in the art will ascertain compositions for controlled or extended release of the pharmaceutical composition. In an aspect, controlled release can be obtained by controlled release compositions and coatings which are known to those of skill in the art. Other controlled release systems are discussed in the review by Langer (Science 249:1527-1533 (1990)) the contents of which are incorporated herein by reference.

Methods of Use/Treatment

According to an embodiment of the invention at least one of the neplanocin derivatives are employed in methods of therapeutic or prophylactic treatment of a subject, which may be referred to as an animal, including a human, against viral infection. As referred to herein, viral infection includes any disease state or condition involving a viral infection. The methods of the invention are suitable for therapeutic or prophylactic viral treatment for various viral infections.

Figures 4, 5A, 5B:
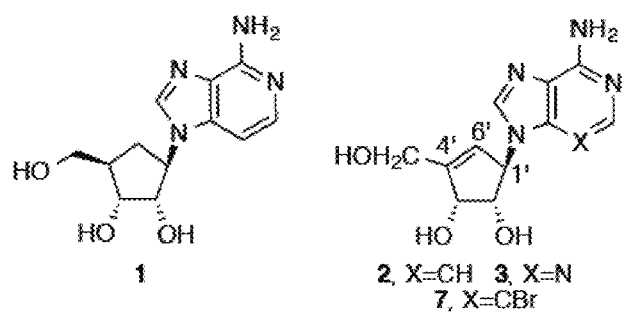
FIG. 4 shows as overview of four families of RNA viruses causing viral hemorrhagic fevers: Arenaviridae, Filoviridae, Bunyaviridae, and Flaviviridae.
FIGS. 5A-C show a mechanism of antiviral activity; exemplary carboxylic nucleosides (shown in FIG. 5A and FIG. 5B) with activity pursuant to SAHase inhibition as depicted in a schematic of cellular enzyme SAHase, which breaks down SAH to adenosine and homocysteine (FIG. 5C).

The compounds and methods disclosed herein can be used to treat viruses within various families of viruses as disclosed herein as part of a pharmaceutically acceptable drug formulation. In an aspect, the neplanocin derivatives are broad spectrum antiviral agents as derivatives are capable of providing antiviral activity to more than one virus or classification of virus. In an aspect, the virus is a DNA or an RNA virus. In an aspect, the RNA virus is a negative strand RNA virus. In a preferred aspect, the virus is human cytomegalovirus (HCMV), measles, filovirus, including Ebola, norovirus (NOV), dengue, vaccinia or HBV. In a most preferred aspect the filovirus virus is an Ebola virus. In a further preferred aspect, the virus is a viral hemorrhagic fever (VHF) virus, referring to a group of febrile illnesses caused by four families of RNA viruses: Arenaviridae, Filoviridae, Bunyaviridae, and Flaviviridae (as depicted in FIG. 4).

Many viruses share biochemical, regulatory, and signaling pathways. Relevant taxonomic families of RNA viruses include, without limitation, Arenaviridae, including for example tacaribe virus and pinchinde virus, Astroviridae, Birnaviridae, Bromoviridae, Bunyaviridae, including for example rift valley fever virus and punta toro virus, Caliciviridae, Closteroviridae, Comoviridae, Coronaviridae, including for example SARS coronavirus, Cystoviridae, Flaviviridae, including for example dengue yellow fever virus, Flexiviridae, including for example dengue virus, west nile virus, yellow fever virus, Japanese encephalitis virus, Hepevirus, including for example human cytomegalovirus and herpes simplex virus 1 and 2, Leviviridae, Luteoviridae, Mononegavirales, Mosaic Viruses, Nidovirales, Nodaviridae, Orthomyxoviridae, including for example influenza virus such as influenza A H1N1 virus, Paramyxoviridae, including for example measles virus (genus Morbillivirus) and respiratory syncytial virus, Picobirnavirus, Picornaviridae, including for example polo virus, Potyviridae, Reoviridae, Retroviridae, Sequiviridae, Tenuivirus, Togaviridae, including for example Venezuelan equine encephalitis virus and chickungunya virus, Tombusviridae, Totiviridae, and Tymoviridae.

Relevant taxonomic families of DNA viruses include, without limitation, Adenoviridae, Hepadnaviridae, Herpesviridae, including for example human cytomegalovirus (HCMV), Papillomaviridae, Papovaviridae, including for example papillomavirus, BK virus, and JC virus, Parvoviridae, and Poxviridae, including for example vaccinia virus, small pox and monkeypox virus.

Still further relevant taxonomic families of viruses include hepatic viruses, including for example hepatitis B virus and hepatitis C virus, norovirus, etc.

By "treating" is meant administering the neplanocin derivatives or pharmaceutical compositions containing the neplanocin derivatives for prophylactic and/or therapeutic purposes. Prophylactic treatment may be administered, for example, to a subject who is not yet ill, but who is susceptible to, or otherwise at risk of, a particular disorder, e.g., infection with a virus. Prophylactic treatment reduces the likelihood of a subject contracting an infection from one or more of the viruses described herein. Therapeutic treatment may be administered, for example, to a subject already suffering from a disorder in order to improve or stabilize the subject's condition (e.g., a patient already infected with a virus). Thus, in the claims and embodiments described herein, treating is the administration to a subject either for therapeutic or prophylactic purposes. In some instances, as compared with an equivalent untreated control, treatment may ameliorate a disorder or a symptom thereof by, e.g., 5%, 10%, 20%, 30%, 40%, 50%, 60%, 70%, 80%, 90%, 95%, or 100% as measured by any standard technique. In some instances, treating can result in the inhibition of viral infection, the treatment of the infection, and/or the amelioration of symptoms of the infection. Confirmation of treatment can be assessed by detecting an improvement in or the absence of symptoms, or by the inability to detect the presence of the virus in the treated subject.

The methods of treatment are also meant to include the administering a therapeutically effective amount of at least one of the neplanocin derivatives or pharmaceutical compositions containing at least one of the neplanocin derivatives to reduce viral replication of the DNA and RNA viruses disclosed herein. In some embodiments, the neplanocin derivatives or pharmaceutical compositions containing the neplanocin derivatives of the present invention can reduce the replication of a virus (kill virus cells (CC50, also referred to as cellular toxicity)) by at least 10%, 20%, 30%, 40%, 50%, 60%, 70%, 80%, 90%, 95% or more.

The methods of the invention may comprise, consist of or consist essentially of administering at least one of the neplanocin derivatives or a pharmaceutical composition containing the neplanocin derivatives to a subject in need of the antiviral therapeutic or prophylactic treatment. As used herein, by "administering" is meant a method of giving a dosage of at least one of the neplanocin derivatives or a pharmaceutical composition containing at least one of the neplanocin derivatives of the invention to an animal generally referred to as a "subject," both of which are herein understood to include human patients. The compositions utilized in the methods described herein can be administered by a route selected from, e.g., parenteral, dermal, transdermal, ocular, inhalation, buccal, sublingual, perilingual, nasal, rectal, topical administration, and oral administration or ingestion. Parenteral administration includes intravenous, intraperitoneal, subcutaneous, intraarterial, intravascular, and intramuscular administration. The preferred method of administration can vary depending on various factors (e.g., the components of the composition being administered and the severity of the condition being treated). In a preferred aspect, the administering is by ingestion, injection, infusion, or other bodily administration.

In an aspect, the dose of neplanocin derivative(s) provided to a subject in need may be administered daily, more than once daily, three times daily, every other day or in a tapered fashion depending upon various factors, including for example, nature of prophylactic versus therapeutic treatment, severity of infection being treated, the patient's overall health, and whether underlying conditions are present. For example, the more severe the infection, the higher the amount of neplanocin derivatives may be required to effectively treat it. It is understood that a physician would be able to monitor and adjust doses, formulations, and application methods as needed based on the patient's symptoms and responses to therapy and within the parameters and dose ranges described in the embodiments of the present invention.

The methods of treatment disclosed herein may be performed alone or in conjunction with another treatment. In an aspect, the methods of treatment may be beneficially combined with other antivirals, including for example, amantadine, rimantadine, gancyclovir, acyclovir, ribavirin, penciclovir, oseltamivir, foscamet zidovudine (AZT), didanosine (ddI), lamivudine (3TC), zalcitabine (ddC), stavudine (d4T), nevirapine, delavirdine, indinavir, ritonavir, vidarabine, nelfinavir, saquinavir, relenza, tamiflu, pleconaril, interferons, etc. The methods of treatment may further be combined with other therapeutic agents, including for example, steroids and corticosteroids such as prednisone, cortisone, fluticasone and glucocorticoid, antibiotics, analgesics, bronchodilators, or other treatments for respiratory and/or viral infections.

The methods of treatment disclosed herein may be performed or provided to a subject, e.g., at home, the doctor's office, a clinic, a hospital's outpatient department, or a hospital. The duration of the therapy depends on the age and condition of the subject, the severity of the subject's infection, and how the subject responds to the treatment; the factors can be determined by one of skill in the art.

Figure 5C:
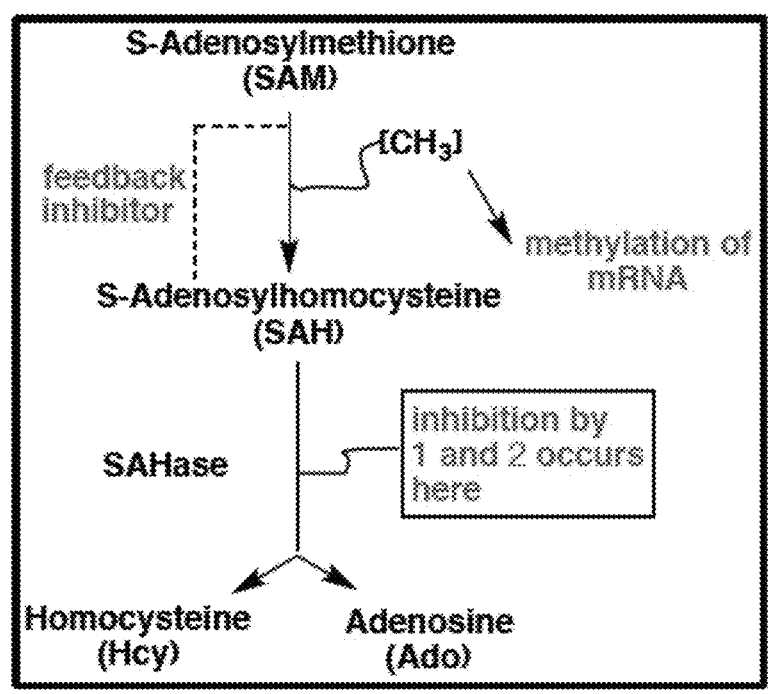
Figure 6:
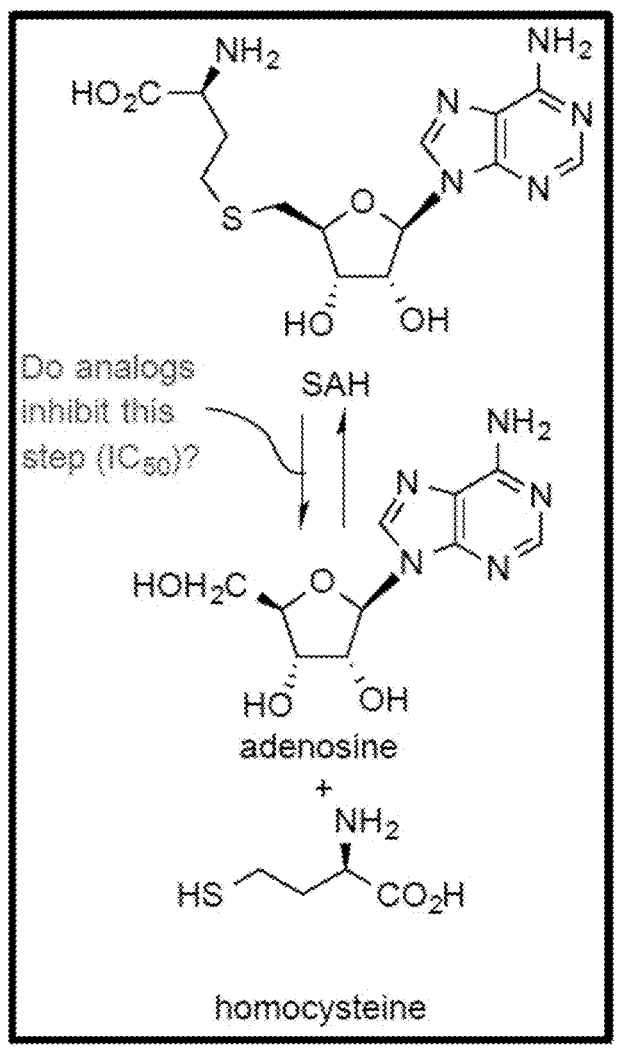
FIG. 6 shows a site of neplanocin derivative inhibition of SAHase and inhibition of SAHase to be quantitated by release of free homocysteine according to an embodiment of the invention where certain neplanocin derivatives have antiviral activity via SAHase inhibition.
Figure 7:
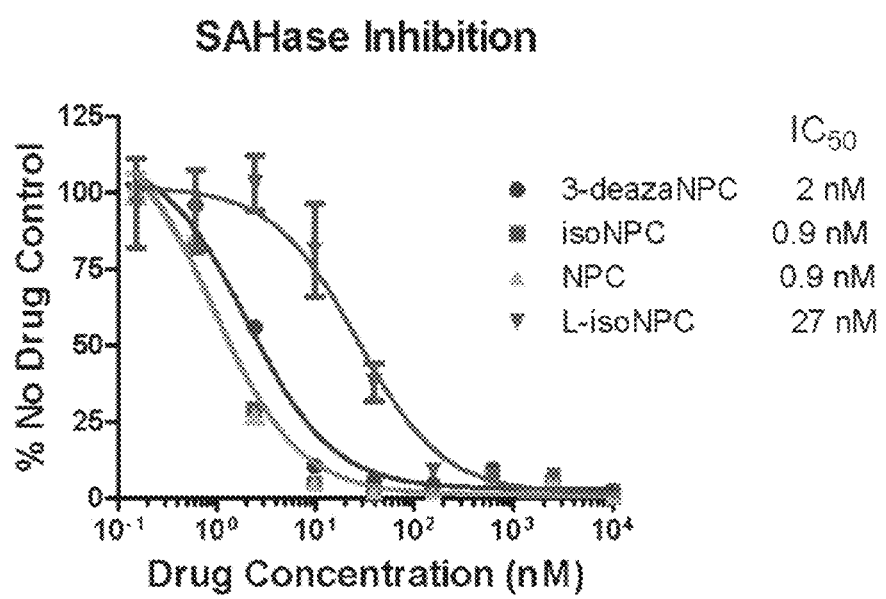
FIG. 7 shows neplanocin analogue SAHase inhibition data.

While an understanding of the mechanism is not necessary to practice the present invention and while the present invention is not limited to any particular mechanism of action, it is contemplated that, in some embodiments, the known SAHase inhibition by neplanocin A provides a source of antiviral activity as inhibition of cellular SAHase is required for modulating essential replicative methylations by S-adenosylmethionine (SAM). In an aspect, neplanocin derivatives based on D-like neplanocin derivatives, such as 3-deazaneplanocin (or other known components such as isteromycin) inhibiting SAHase activity provide a beneficial mechanism of antiviral activity as shown in FIGS. 5A-C.

In an aspect, the neplanocin derivatives according to the invention employed in the methods of treatment disclosed herein provide a $IC_{50} \leq 5.0$ μM. In a further aspect, the neplanocin derivatives employed in the methods of treatment disclosed herein provide a $IC_{50} \leq 5.0$ μM while maintaining a selectivity index $(CC_{50}/IC_{50}) \geq 10$. In some aspects, neplanocin derivatives screened against SAHase inhibitory assays having an $IC_{50} \leq 10.0$ nM provide antiviral efficacy according to an SAHase inhibition mechanism.

In other aspects, and without being limited to a particular mechanism of action, neplanocin derivatives, namely L-like enantiomers, employed in the methods of treatment disclosed herein provide a weak SAHase inhibition indicating an alternative mechanism of antiviral activity. The alternative mechanism of action, proposed to involve the C4 center (defined above in neplanocin derivatives as Y), namely $CH_2OH$ for the D-3-Deazaisoneplanocin analogues, provides a further benefit of circumventing viral resistance due to a distinct mechanism of antiviral action. As disclosed herein, in an aspect of the invention, it is an unexpected benefit of the claimed invention that certain neplanocin derivatives having less inhibitory effect against SAHase also unexpectedly provide antiviral efficacy demonstrating an additional and previously unknown antiviral mechanism of action, such as for example substrate affinity for kinases (e.g. adenosine, deoxycytidine). In a preferred aspect, L-like isoneplanocin derivatives (or pharmaceutically-acceptable prodrug precursors and salts thereof) provide reduced SAHase inhibition in comparison to neplanocin A or D-like isoneplanocin while providing antiviral efficacy. In an aspect, reducued SAHase inhibition is indicated by an $IC_{50} \geq 10.0$ nM. Without being limited to a particular mechanism of action, beneficially, as disclosed pursuant to the present invention, antiviral neplanocin derivatives, particularly L-like isoneplanocin derivatives (or pharmaceutically-acceptable prodrug precursors and salts thereof) may provide decreased SAHase inhibition allowing cellular mRNA cap methylation and full protein synthesis and thereby providing antiviral efficacy without general toxicity.

In an aspect, the use of enantiomer neplanocin derivatives provides a pair of potent antiviral agents as a result of distinct mechanisms of action for antiviral activity. In such an aspect, the methods of treatment disclosed herein may include a combination of enantiomer neplanocin derivatives.

In an aspect, neplanocin derivatives having reduced SAHase inhibitory effects and maintained antiviral activity are employed to provide antiviral prophylaxis or treatment without SAHase inhibition-induced general toxicity. In a preferred aspect, the neplanocin derivative having the following L-like isoneplanocin formula is administered to a subject in need of antiviral therapeutic or prophylactic treatment, such as for example an Ebola virus:

Wherein R is a hydrogen or a hydroxyl group, halogen, or $C_1$-$C_4$ alkyl optionally substituted with a hydroxyl group (or combination of the same such that R is the same or is different), wherein Y is a hydrogen, a hydroxyl group, $CH_2OH$, $CH_2NH_2$ (NHR, NRR', wherein the R and R' in NHR and NRR' are alkyl, aryl or araalkyl), $CH_2X$ (wherein X is a halogen), or a $C_1$-$C_4$ alkyl optionally substituted with a hydroxyl group, and wherein X is $NH_2$, NHR, NRR', NHOH, or hydrogen (wherein the R and R' in NHR and NRR' are alkyl, aryl or araalkyl); or pharmaceutically-acceptable prodrug precursors and salts thereof. It is unexpected that the L-like isoneplanocin analogue provides antiviral efficacy, including for filovirus, including Ebola, despite the reduced SAHase inhibitory effect, which is a known mechanism of antiviral activity.

In a further aspect, deazaneplanocin derivatives, including D- and L-like 1',6'-iso-3-deazaneplanocin (or pharmaceutically-acceptable prodrug precursors and salts thereof), provide reduced SAHase inhibition in comparison to neplanocin A or D-like isoneplanocin while providing antiviral efficacy.

In an aspect, neplanocin derivatives having the following formulae are administered to a subject in need of antiviral therapeutic or prophylactic treatment, such as for example an Ebola virus or any viral hemorrhagic fever (VHF):

L-Isoneplanocin Analogue
Wherein R is a hydrogen or a hydroxyl group, halogen, or $C_1$-$C_4$ alkyl optionally substituted with a hydroxyl group, X is $NH_2$, NHR, NRR', NHOH, or hydrogen (wherein the R and R' in NHR and NRR' are alkyl, aryl or araalkyl), and Y is a hydrogen, a hydroxyl group, $CH_2OH$, $CH_2NH_2$ (NHR, NRR', (wherein the R and R' in NHR and NRR' are alkyl, aryl or araalkyl)), $CH_2X$ (wherein X is a halogen), or a $C_1$-$C_4$ alkyl optionally substituted with a hydroxyl group; or pharmaceutically-acceptable prodrug precursors and salts thereof.

D-3-Deazaisoneplanocin Analogue

L-3-Deazaisoneplanocin Analogue
Wherein R2' is a hydrogen or a hydroxyl group, halogen, or $C_1$-$C_4$ alkyl optionally substituted with a hydroxyl group, R3' is a hydrogen or a hydroxyl group, halogen, or $C_1$-$C_4$ alkyl optionally substituted with a hydroxyl group, R6' is a hydrogen or halogen (preferably F), W is a hydrogen or a halogen (preferably F), X is $NH_2$, NHR, NRR', NHOH, or hydrogen (wherein the R and R' in NHR and NRR' are alkyl, aryl or araalkyl), Y is a hydrogen, a hydroxyl group, $CH_2OH$, $CH_2NH_2$ (NHR, NRR', (wherein the R and R' in NHR and NRR' are alkyl, aryl or araalkyl)), $CH_2X$ (wherein X is a halogen), or a $C_1$-$C_4$ alkyl optionally substituted with a hydroxyl group, and Z is a hydrogen, halogen (preferably a F or Br), alkyl or substituted alkyl, cyano and derivatives therefrom; or pharmaceutically-acceptable prodrug precursors and salts thereof.

The methods of treatment employing the neplanocin derivatives for treatment of viral hemorrhagic fevers (VHF) result in reduced viral replication and reduced or elimination of symptoms of the viral infections, including for example, fever, increased vascular permeability, and coagulation defects causing severe bleeding and death. The methods for treatment of VHF are highly beneficial as there are currently no vaccines (excluding for yellow fever) or drug candidates capable of treating VHF outbreaks. In an aspect of the invention, the neplanocin derivatives, including isoneplanocins, deazaneplanocins, and deazaisoneplanocins provide broad-spectrum effectiveness towards the VHF as a result of the unexpected, distinct mechanisms of antiviral effectiveness provided by the neplanocin derivatives, namely 1,6-isomers of neplanocin A and 1,6-deazaisomers of neplanocin A. It is a further benefit of the methods of treatment that the distinct mechanisms of antiviral efficacy reduce the ability of VHF to develop drug resistance. It is a still further benefit of the methods of treatment that a combination of neplanocin derivatives can be employed to take advantage of the distinct mechanisms of antiviral efficacy.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

General Materials and Methods

Melting points were recorded on a Meltemp II melting point apparatus and the values were uncorrected. $^1$H and $^{13}$C NMR spectra were recorded on either a Bruker AC 600 spectrometer (600 MHz for proton and 150 MHz for carbon) or a Bruker AV 400 spectrometer (400 MHz for proton and 100 MHz for carbon), referenced to internal tetramethylsilane (TMS) at 0.0 ppm. The mass spectral data was determined using a Waters Micromass Q-TOF Premier Mass Spectrometer. The reactions were monitored by thin-layer chromatography (TLC) using 0.25 mm Whatman Diamond silica gel 60-$F_{254}$ precoated plates with visualization by irradiation with a Mineralight UVGL-25 lamp. Column chromatography was performed on Whatman silica, 230-400 mesh, and 60 Å using elution with the indicated solvent system. Yields refer to chromatographically and spectroscopically ( $^1$H and $^{13}$C NMR) homogeneous materials.

Example 1

Synthesis of D-Isoneplanocin.

Step 1: Synthesis of (1S,2R,3S,5R)-2-((Benzyloxy) methyl)-3-((4-methoxybenzyl)oxy)-6-oxabicyclo [3.1.0]-hexane 5

A solution of cyclopentyl epoxide 4 (See Ludek & Meier, Synthesis 2003, 13, 2101; Biggadkike et al., J. Chem. Soc., Perkin Trans, 1 1998, 549) (1.12 g, 5.08 mmol) in THF (20 mL) was treated with NaH (60%, 224 mg, 6.10 mmol) at 0° C. The reaction mixture was allowed to stir at room temperature for an additional 30 min. and 4-methoxylbenzyl bromide (0.72 mL, 5.59 mmol) and tetrabutylammonium iodide (20 mg, 0.05 mmol) were added. After 24 h, the reaction mixture was quenched with saturated $NH_4Cl$ solution and extracted with EtOAc. The organic layer was dried ($Na_2SO_4$), filtered and the solvent was removed by rotary evaporation. The pure product (1.65 g, 95%) was isolated using column chromatography (2:1, hexanes/EtOAc) as a clear liquid: $^1$H NMR (400 MHz, $CDCl_3$) d ppm 7.30-7.24 (m, 5H), 7.20 (d, J=8.8 Hz, 2H), 6.81 (d, J=8.8 Hz, 2H), 4.46 (s, 2H), 4.38 (d, J=2.7 Hz, 2H), 3.86 (d, J=7.3 Hz, 1 H), 3.75 (s, 3H), 3.50 (m, 1 H), 3.43 (d, J=2.6 Hz, 1 H), 3.37 (m, 2H), 2.57 (t, J=5.9 Hz, 1 H), 2.13 (m, 1 H), 2.03 (m, 1 H); $^{13}$C NMR (100 MHz, $CDCl_3$) dppm 159.0, 138.0, 130.4, 129.3, 128.4, 127.6, 113.8, 80.5, 73.1, 70.4, 69.2,60.3, 59.6, 57.9, 55.2, 47.4, 37.8. HRMS calculated for $C_{21}H_{24}O_4Na$ $[M+Na]^+$: 363.1572; found 363.1564.

Step 2: Synthesis of (1R,4S,5S)-5-(Benzyloxy) methyl)-4-((4-methoxybenzyl)oxy)cyclopent-2-enol 6

To a solution of (1S,2R,3S,5R)-2-(Benzyloxy)methyl)-3-((4-methoxybenzyl)oxy)-6-oxabicyclo[3.1.0]-hexane 5 (450 mg, 1.32 mmol) in THF (40 mL), lithium hexamethyldisilazide (7 mL, 1.0 M in THF, 7 mmol) was added dropwise at room temperature. The reaction mixture was heated at 60° C. for 3 h. The resulting solution was cooled to room temperature, quenched with saturated $NH_4Cl$ solution and extracted with EtOAc. The organic phases were combined, washed with brine, dried ($Na_2SO_4$) and concentrated under reduced pressure. The crude residue was purified by column chromatography (1:1, EtOAc/hexanes) to give 6 (380 mg, 84%) as a yellow liquid: $^1$H NMR (600 MHz, $CDCl_3$) dppm 7.33-7.29 (m, 5H), 7.22 (d, J=8.4 Hz, 2H), 6.83 (d, J=8.4 Hz, 2H), 5.91 (s, 2H), 4.53-4.46 (m, 4H), 4.42 (d, J=4.3 Hz, 1 H), 4.24 (d, J=4.6 Hz, 1 H), 3.76 (s, 3H), 3.58 (m, 2H), 2.77 (br, 1 H), 2.26 (m, 1 H); $^{13}$C NMR (150 MHz, $CDCl_3$) d ppm 159.2, 138.3, 136.2, 133.2, 130.6, 129.4, 128.4, 127.70, 127.68, 113.8, 83.6, 77.8, 73.2, 70.1, 70.0, 55.8, 55.3. HRMS calculated for $C_{21}H_{24}O_4Na$ $[M+Na]^+$: 363.1572; found 363.1577.

Step 3: Synthesis of (1S,2S,3S,4R, 5R)-3-(Benzyloxy)methyl)-4-((4-methoxybenzyl)oxy)-6-oxabicyclo[3.1.0]hexan-2-ol 7

To a solution of (1R,4S,5S)-5-(Benzyloxy)methyl)-4-((4-methoxybenzyl)oxy)cyclopent-2-enol (220 mg, 0.65 mmol) in $CH_2Cl_2$ (20 mL) was added mCPBA (335 mg, 77%, 1.5 mmol) at 0° C. This mixture was stirred overnight and quenched with sodium bisulfite. The reaction mixture was diluted with $CH_2Cl_2$ and washed with $NaHCO_3$, brine, dried ($Na_2SO_4$) and concentrated under reduced pressure. The crude residue was purified by column chromatography (1:1, EtOAc/hexanes) to give 7 (380 mg, 84%) as a white solid, mp 72-73° C.; $^1$H NMR (400 MHz, $CDCl_3$) dppm 7.32-7.24 (m, 7H), 6.85 (d, J=8.3 Hz, 2H), 4.61 (d, J=11.7 Hz, 1 H), 4.48 (dd, J=11.8, 15.6 Hz, 2H), 4.39 (d, J=11.9 Hz, 1 H), 4.03 (d, J=7.9 Hz, 1 H), 3.76 (s, 3H), 3.65 (dd, J=2.7, 9.4 Hz, 1 H), 3.50 (m, 3H), 2.69 (br, 1 H), 1.80 (m, 1 H); $^{13}$C NMR (100 MHz, $CDCl_3$) dppm 159.3, 138.2, 130.2, 129.4, 128.3 (2C), 127.6, 113.8, 77.0, 73.1, 71.8, 71.1, 66.9, 56.7, 55.2, 54.5, 44.9. HRMS calculated. for $C_{21}H_{24}O_5Na$ $[M+Na]^+$: 379.1521; found 379.1511.

Step 4: Synthesis of (1S,2R,3S,4S,5R)-2-(6-Amino-9H-purin-9-yl)-4-((benzyloxy)methyl)-5_((4-methoxybenzyl) oxy)cyclopentane-1,3-diol 8

Adenine (1.23 g, 9.1 mmol) and (1S,2S,3S,4R,5R)-3-(Benzyloxy)methyl)-4-((4-methoxybenzyl)oxy)-6-oxabicyclo[3.1.0]hexan-2-ol (1.30 g, 3.65 mmol) were suspended in DMF (20 mL) under $N_2$ for 15 min. at room temperature. 1,8-Diazabicyclo[5.4.0]undec-7-ene (DBU, 1.64 mL, 10.9 mmol) was added and the reaction mixture was heated at 90° C. for 8 h. After the reaction was cooled to room temperature, the resulting solid was removed by filtration over Celite and then rinsed with $CH_2Cl_2$. The filtrate was evaporated under reduced pressure and the residue purified by column chromatography to afford 8 (900 mg, 50%) as white solid (20:1, $CH_2Cl_2$/MeOH): m.p. 163-165° C.: $^1H$ NMR (400 MHz, DMSO) dppm 8.13 (s, 1H), 8.10 (s, 1H), 7.36-7.27 (m, 7H), 7.16 (s, 2H), 6.87 (d, J=8.7 Hz, 2H), 5.83 (d, J=5.4 Hz, 1H), 5.06 (d, J=7.1 Hz, 1H), 4.61-4.50 (m, 6H), 4.27 (m, 1H), 3.76-3.73 (m, 4H), 3.58 (dd, J=4.2, 9.4 Hz, 1 H), 3.51 (m, 1H), 2.10 (m, 1H); $^{13}C$ NMR (100 MHz, DMSO) dppm 158.7, 156.1, 152.0, 149.9, 141.2, 138.6, 130.8, 129.3, 128.3, 127.5, 127.4, 119.6, 113.6, 77.8, 72.2, 71.1, 70.5, 70.3, 69.2, 67.6, 55.1, 50.7. HRMS calculated for $C_{26}H_{30}N_5O_5$ $[M+H]^+$: 492.2247; found 492.2241.

Step 5: Synthesis of (1R,2S,3R,4S,5S)-3-(6-Amino-9H-purin-9-yl)-5-((benzyloxy)methyl)-cyclopentane-1,2, 4-triol 10

To a solution of (1S,2R,3S,4S,5R)-2-(6-Amino-9H-purin-9-yl)-4-((benzyloxy)methyl)-5-((4-methoxybenzyl)oxy)cyclopentane-1,3-diol (100 mg, 0.20 mmol) in MeOH (2 mL) was added 1N HCl (2 mL) and the solution was stirred at 50° C. for 4 h. The solvent was removed under reduced pressure to give 10 (70 mg, 94%) as white solid that was used directly in this form in the next step. $^1H$ NMR (600 MHz, MeOD) d ppm 8.59 (s, 1H), 8.44 (s, 1H), 7.42-7.29 (m, 5H), 4.89 (m, 1H), 4.63 (m, 3H), 4.53 (m, 1 H), 4.17 (m, 1 H), 3.76 (m, 2H), 2.23 (m, 1H). HRMS calculated for $C_{18}H_{22}N_5O_3$ $[M+H]^+$: 372.1672; found 372.1666.

Step 6: Synthesis of (3αS,4R,5S,6S,6αR)-4-(6-Amino-9H-purin-9-yl)-6-((benzyloxy)methyl)-2,2-dimethyltetrahydro-3αH-cyclopenta [d] [1,3]dioxol-5-ol 11

To a solution of (1R,2S,3R,4S,5S)-3-(6-Amino-9H-purin-9-yl)-5-((benzyloxy)methyl)-cyclopentane-1,2,4-triol (70 mg, 0.19 mmol) in acetone (5 mL) was added triethyl orthoformate (0.25 mL, 1.50 mmol) and p-TsOH•$H_2O$ (65 mg, 0.33 mmol). The reaction mixture was stirred at room temperature for 4 h, quenched with saturated $NaHCO_3$ solution (10 mL) and extracted with EtOAc. The combined organic phases were dried ($Na_2SO_4$), filtered and evaporated under reduced pressure. The residue was purified via column chromatography (20:1, EtOAc/MeOH) to give 11 (60 mg, 77%) as a white foam: $^1H$ NMR (400 MHz, $CDCl_3$) dppm 8.26 (s, 1 H), 8.00 (s, 1H), 7.36-7.24 (m, 5H), 5.80 (s, 2H), 4.80 (t, J=7.02 Hz, 1 H), 4.70-4.63 (m, 2H), 4.60 (s, 2H), 4.42 (dd, J=6.8, 9.6 Hz, 1H), 3.78 (m, 2H), 2.50 (m, 1H), 1.61 (s, 3H), 1.38 (s, 3H); $^{13}C$ NMR (100 MHz, $CDCl_3$) dppm 155.6, 152.0, 149.4, 140.6, 137.9, 128.3, 127.6, 119.3, 113.3, 79.6, 77.9, 73.3, 73.2, 69.3, 67.9, 50.1, 27.1, 24.8. HRMS calculated for $C_{21}H_{26}N_5O_4$ $[M+H]^+$: 412.1985; found 412.1975.

Step 7: Synthesis of (3αS,4S,5S,6R,6αR)-4-(6-Amino-9H-purin-9-yl)-6-99benzyloxy)methyl)-2,2-dimethyltetrahydro-3αH-cyclopenta[d] [1,3]dioxol-5-yl methanesulfonate 12

To a solution of (3aS,4R,5S,6S,6aR)-4-(6-Amino-9H-purin-9-yl)-6-((benzyloxy)methyl)-2,2-dimethyltetrahydro-3aH-cyclopenta[d][1,3]dioxol-5-ol (90 mg, 0.22 mmol) in anhydrous $CH_2Cl_2$ (20 mL) were added, dropwise, triethylamine (0.06 mL, 0.44 mmol), methanesulfonyl chloride (0.02 mL, 0.26 mmol) and 4-dimethylaminopyridine (5 mg, 0.04 mmol) at 0° C. under $N_2$. The mixture was stirred at room temperature overnight. The reaction mixture was quenched with saturated $NaHCO_3$ solution and extracted with $CH_2Cl_2$. The organic phases were dried ($Na_2SO_4$). The residue, after filtration and evaporation, was loaded onto silica gel. Column chromatography (30:1, EtOAc/MeOH) afforded 12 (100 mg, 93%) as a white foam: $^1H$ NMR (400 MHz, $CDCl_3$) dppm 8.32 (s, 1H), 7.84 (s, 1H), 7.41-7.34 (m, 5H), 6.28 (s, 2H), 5.78 (t, J=9.2 Hz, 1H), 5.15 (m, 1H), 4.82 (ddd, J=9.3, 8.0, 5.6 Hz, 2H), 4.61 (s, 2H), 3.83 (dd, J=9.7, 4.0 Hz, 1H), 3.76 (dd, J=9.7, 4.0 Hz, 1H), 2.63-2.55 (m, 1H), 2.53 (s, 3H), 1.59 (s, 3H), 1.30 (s, 3H); $^{13}C$ NMR (100 MHz, $CDCl_3$) dppm 155.8, 152.3, 149.9, 140.5, 137.8, 128.5, 127.9, 127.8, 120.3, 113.5, 81.2, 79.2, 77.5, 73.5, 66.9, 66.7, 49.1, 37.5, 27.5, 25.1. HRMS calculated for $C_{22}H_{28}N_5O_6S$ $[M+H]^+$: 490.1760; found 490.1782.

Step 8: Synthesis of 9-((3αS,6R,6αR)-6-((Benzyloxy)methyl)-2,2-dimethyl-6,6α-dihydro-3αH-cyclopenta[d] [1,3]dioxol-4-yl) -9H-purin-amine 13

To a solution of (3 aS,4S,5S,6R,6aR)-4-(6-Amino-9H-purin-9-yl)-6-99benzyloxy)methyl)-2,2-dimethyltetrahydro-3aH-cyclopenta[d][1,3]dioxol-5-yl methanesulfonate (70 mg, 0.14 mmol) in THF (5 mL) was added sodium methoxide (25 mg, 0.46 mmol) in MeOH (0.5 mL) and the reaction mixture was refluxed for 4 h. The residue, after evaporation under reduced pressure, was loaded onto silica gel, which was then added to a column for chromatographic purification (50:1, EtOAc/MeOH) to afford 13 (50 mg, 89%) as white solid, mp 187-188° C.: $^1H$ NMR (400 MHz, $CDCl_3$) dppm 8.40 (s, 1H), 8.26 (s, 1H), 7.33-7.28 (m, 5H), 6.70 (d, J=2.7 Hz, 1H), 6.16 (s, 2H), 5.53 (dd, J=5.8, 1.1 Hz, 1H), 4.73 (d, J=5.8 Hz, 1 H), 4.54 (s, 2H), 3.69 (dd, J=9.4, 4.6 Hz, 1H), 3.48 (dd, J=9.4, 6.1 Hz, 1H), 3.25 (m, 1H), 1.42 (s, 3H), 1.41 (s, 3H); $^{13}C$ NMR (100 MHz, $CDCl_3$) dppm 155.5, 153.4, 150.1, 138.7, 138.6, 135.3, 128.4, 127.7, 127.6, 119.8, 119.2, 111.6, 82.9, 80.6, 73.2, 70.6, 50.1, 27.4, 25.9. HRMS calculated for $C_{21}H_{24}N_5O_3$ $[M+H]^+$: 394.1879; found 394.1873.

Step 9: Synthesis of ((3αR,4R,6αS)-6-(6-Amino-9H-purin-9-yl)-2,2-dimethyl-4,6α-dihydro-3αH-cyclopenta[d] [1,3]dioxol-4-yl)methanol 14

A solution of 9-((3aS,6R,6aR)-6-(Benzyloxy)methyl)-2, 2-dimethyl-6,6a-dihydro-3aH-cyclopenta[d][1,3]dioxol-4-yl)-9H-purin-amine (300 mg, 0.76 mmol) and 20% $Pd(OH)_2$/C (375 mg) in cyclohexene (5 mL) and EtOH (8 mL) was heated at reflux for 12 h and then filtered through Celite. The filtrate was evaporated to dryness under reduced pressure and purified by column chromatography (9:1, EtOAc/MeOH) to give 14 (200 mg, 87%) as a white solid. $^1H$ NMR (400 MHz, MeOD) dppm 8.34 (s, 1H), 8.26 (s, 1H), 6.60 (d, J=2.7 Hz, 1H), 5.65 (dd, J=1.2, 5.8 Hz, 1H), 4.75 (d, J=5.6 Hz, 1H), 4.62 (br, 1H, OH), 3.77 (dd, J=4.9, 11.1 Hz, 1H), 3.63 (dd, J=5.8, 11.1 Hz, 1H), 3.09 (m, 1H), 1.42 (s, 3H), 1.38 (s, 3H); $^{13}C$ NMR (100 MHz, MeOD) dppm 157.6, 154.5, 151.0, 140.4, 137.1, 121.3, 120.5, 112.6, 84.1, 81.9, 64.0, 53.8, 27.8, 26.0. HRMS calculated for $C_{14}H_{18}N_5O_3$ $[M+H]^+$: 304.1410; found 304.1411.

Step 10: Synthesis of "D"-Isoneplanocin; (1R,2S, 5R)-3-(6-Amino-9H-purin-9-yl)-5-(hydroxymethyl) cyclopent-3-ene-1,2-diol 2

To a solution of ((3aR,4R,6aS)-6-(6-Amino-9H-purin-9-yl)-2,2-dimethyl-4,6a-dihydro-3aH-cyclopenta[d][1,3]dioxol-4-yl)methanol (190 mg, 0.63 mmol) in MeOH (2 mL) was added 2N HCl (5 mL) and the reaction mixture was stirred at room temperature for 4 h. The solution was then neutralized with IRA-67 resin and the filtrate was evaporated to give 2 (150 mg, 90%) as a pale white solid, mp 195-196° C.: $^1$H NMR (600 MHz, D$_2$O) dppm 8.00 (s, 1H), 7.83 (s, 1H), 6.17 (d, J=2.1 Hz, 1H), 4.86 (dd, J=1.3, 5.9 Hz, 1H), 4.09 (t, J=5.8 Hz, 1H), 3.76 (dd, J=4.6, 11.5 Hz, 1H), 3.63 (dd, J=5.5, 11.5 Hz, 1H), 2.87 (m, 1H); $^{13}$C NMR (150 MHz, D$_2$O) dppm 154.9, 152.3, 147.8, 139.5, 134.5, 123.6, 117.8, 73.0, 71.0, 61.0, 22 9 50.8. HRMS calculated for C$_{11}$H$_{14}$N$_5$O$_3$ [M+H]$^+$: 264.1097; found 264.1093. [a]$^{22.9}$$_D$ 38.5° (c 0.18, H$_2$O).

The synthesis methods for D-isoneplanocin required distinct pathway and separation of enantiomer compounds resulting in separate synthesis pathway to generate the more preferred enantiomer L-isoneplanocin.

Example 2

Synthesis of L-Isoneplanocin.

Steps 1-3: The procedure outlined in Example 1, steps 1-3 for the preparation of (1S,2S,3S,4R,5R)-3-(Benzyloxy)methyl)-4-((4-methoxybenzyl)oxy)-6-oxabicyclo[3.1.0]hexan-2-ol 7.

Step 4: Synthesis of (1S,2R,3R,4R,5S)-3-(6-Amino-9H-purin-9-yl)-5-((benzyloxy)methyl)-4-((4-methoxybenzyl)oxy)cyclopentane-1,2-diol 9

Adenine (1.23 g, 9.1 mmol) and (1S,2S,3S,4R,5R)-3-(Benzyloxy)methyl)-4-((4-methoxybenzyl)oxy)-6-oxabicyclo[3.1.0]hexan-2-ol (1.30 g, 3.65 mmol) were suspended in DMF (20 mL) under N$_2$ for 15 min. at room temperature. 1,8-Diazabicyclo[5.4.0]undec-7-ene (DBU, 1.64 mL, 10.9 mmol) was added and the reaction mixture was heated at 90° C. for 8 h. After the reaction was cooled to room temperature, the resulting solid was removed by filtration over Celite and then rinsed with CH$_2$Cl$_2$. The filtrate was evaporated under reduced pressure and the residue purified by column chromatography to afford 9 (550 mg, 31%) as white foam (10:1, CH$_2$Cl$_2$/MeOH, respectively): $^1$H NMR (600 MHz, MeOD) d ppm 8.07 (s, 1H), 7.96 (s, 1H), 7.42-7.30 (m, 5H), 6.69 (d, J=8.2 Hz, 2H), 6.47 (d, J=8.5 Hz, 2H), 4.72 (t, J=9.0 Hz, 1H), 4.58 (m, 3H), 4.41 (t, J=7.1 Hz, 1H), 4.28 (d, J=12.1 Hz, 1H), 4.18 (d, J=12.1 Hz, 1H), 4.04 (m, 1H), 3.63 (m, 5H), 2.31 (m, 1H); $^{13}$C NMR (150 MHz, MeOD) dppm 160.6, 157.1, 153.2, 150.9; 142.9, 139.9, 131.0, 130.5, 129.5, 129.1, 128.9, 120.9, 114.3, 78.6, 74.4, 73.4, 72.9, 72.6, 70.8, 68.7, 55.7, 52.7. HRMS calculated for C$_{26}$H$_{30}$N$_5$O$_5$ [M+H]$^+$: 492.2247; found 492.2243.

Step 5: Synthesis of 9-((3αR,4S,5R,6R,6αS)-6-((Benzyloxymethyl)-5-((4-methoxybenzyl)oxy)-2,2-dimethyltetrahydro-3αH-cyclopenta [d] [1,3]dioxol-4-yl)-9H-purin-6-amine 15

To a solution of (1S,2R,3R,4R,5S)-3-(6-Amino-9H-purin-9-yl)-5-((benzyloxy)methyl)-4-((4-methoxybenzyl)oxy) cyclopentane-1,2-diol (90 mg, 0.18 mmol) in acetone (5 mL) was added triethyl orthoformate (0.18 mL, 1.08 mmol) and p-TsOH•H$_2$O (41 mg, 0.21 mmol). The reaction mixture was stirred at room temperature for 4 h, quenched with saturated NaHCO$_3$ solution (10 mL) and extracted with EtOAc. The combined organic phases were dried (Na$_2$SO$_4$), filtered and evaporated under reduced pressure. The resulting residue was purified via column chromatography (20:1, EtOAc/MeOH) to give 15 (80 mg, 84%) as a white foam: $^1$H NMR (400 MHz, CDCl$_3$) d ppm 8.26 (s, 1H), 7.71 (s, 1H), 7.40-7.31 (m, 5H), 6.71 (d, J=8.7 Hz, 2H), 6.52 (d, J=8.7 Hz, 2H), 6.03 (s, 2H), 5.10 (m, 1H), 4.76-4.70 (m, 3H), 4.69-4.63 (m, 2H), 4.15 (d, J=11.6 Hz, 1H), 4.00 (d, J=11.6 Hz, 1H), 3.76 (dd, J=3.6, 9.6 Hz, 1H), 3.70-3.64 (m, 4H), 2.37 (m, 1H), 1.54 (s, 3H), 1.28 (s, 3H); $^{13}$C NMR (100 MHz, CDCl$_3$) dppm 159.1, 155.5, 152.4, 149.6, 140.9, 138.1, 129.5, 129.1, 128.4, 127.72. 127.69, 120.5, 113.3, 112.9, 78.63, 78.60, 77.4, 73.2, 72.8, 68.5, 67.6, 55.1, 50.1, 27.5, 25.0. HRMS calculated for C$_{29}$H$_{34}$N$_5$O$_5$ [M+H]$^+$: 532.2560; found 532.2568.

Step 6: Synthesis of (3αR,4S,5R,6R,6αS)-4-(6-Amino-9H-purin-9-yl)-6-((benzyloxy)methyl)-2,2-dimethyltetrahydro-3αH-cyclopenta [d] [1,3]dioxol-5-ol 16

To a solution of 9-((3aR,4S,5R,6R,6aS)-6-((Benzyloxymethyl)-5-((4-methoxybenzyl)oxy)-2,2-dimethyltetrahydro-3aH-cyclopenta[d][1,3]dioxol-4-yl)-9H-purin-6-amine (70 mg, 0.13 mmol) in CH$_2$Cl$_2$/H$_2$O (20:1, 5 mL) was added 2,3-dichloro-5,6-dicyano-1,4-benzoquinone (60 mg, 0.26 mmol) at 0° C. After 5 h, the reaction mixture was poured into saturated NaHCO$_3$, extracted with CH$_2$Cl$_2$ and the organic layers combined, dried (Na$_2$SO$_4$), filtered and evaporated under reduced pressure. The residue was purified via column chromatography (20:1, EtOAc/MeOH) to give 16 (50 mg, 93%) as a white solid, mp 172-174° C. HRMS calculated for C$_{21}$H$_{26}$N$_5$O$_4$ [M+H]$^+$: 412.1985; found 412.1966.

Step 7: Synthesis of (3αR,4R,5R,6S,6αS)-4-(6-Amino-9H-purin-9-yl)-6-((benzyloxy)methyl)-2,2-dimethyltetrahydro-3αH-cyclopenta [d] [1,3]dioxol-5-yl methansulfonate 17

Following the procedure for the preparation of 12, compound 17 was obtained from 16 (220 mg, 0.54 mmol) as a white foam (240 mg, 90%). The $^1$H and $^{13}$C NMR spectroscopic measurements were consistent with that reported above for 12. HRMS calculated for C$_{22}$H$_{28}$N$_5$O$_6$S [M+H]$^+$: 490.1760; found 490.1782.

Step 8: Synthesis of 9-((3αR,6S,6αS)-6-((Benzyloxy)methyl)-2,2-dimethyl-6,6α-dihydro-3αH-cyclopenta[d] [1,3]dioxol-4-yl) -9H-purin-6-amine 18

Following the procedure for the preparation of 13, compound 18 was obtained from 17 (210 mg, 0.42 mmol) as a white solid (150 mg, 90%). The $^1$H and $^{13}$C NMR spectroscopic measurements were consistent with that reported above for 13. HRMS calculated for C$_{21}$H$_{24}$N$_5$O$_3$ [M+H]$^+$: 394.1879; found 394.1848.

Step 9: Synthesis of ((3αS,4S,6αS)-6-(6-Amino-9H-purin-9-yl)-2,2-dimethyl-4,6α-dihydro-3αH-cyclopenta[d] [1,3]dioxol-4-yl)methanol 19

Following the procedure for the preparation of 14, compound 19 was obtained from 18 (120 mg, 0.30 mmol) as a white solid (80 mg, 87%). The $^1$H and $^{13}$C NMR spectroscopic measurements were consistent with that reported above for 14. HRMS calculated for $C_{14}H_{18}N_5O3$ [M+H]$^+$: 304.1410; found 304.1401.

Step 10: Synthesis of "L"-Isoneplanocin; (1S,2R, 5S)-3-(6-Amino-9H-purin-9-yl)-5-(hydroxymethyl) cyclopent-3-ene-1,2-diol 3

Following the procedure for the preparation of 2, compound 3 was obtained from 19 (70 mg, 0.23 mmol) as a white solid (56 mg, 92%), mp 191-193 ° C. The $^1$H and $^{13}$C NMR spectroscopic measurements were consistent with that reported above for 2. HRMS calculated for $C_{11}H_{14}N_5O_3$ [M+H]$^+$: 264.1097; found 264.1090. $[\alpha]^{23.0}_D$ –32.8° (c 0.04, $H_2O$).

The synthesis methods for L-isoneplanocin beneficially arrived at the preferred enantiomer. However, distinct synthesis pathway employing alternative starting materials would be preferred to preferentially generate a single enantiomer without requiring separation of the enantiomer.

Example 3

Antiviral Activities of "D"-Isoneplanocin and "L"-Isoneplanocin

"D"-Isoneplanocin and "L"-Isoneplanocin synthesized in examples 1 and 2, respectively, were evaluated against both DNA and RNA viruses to address their efficacy in reducing viral replication. The compound concentration resulting in 50% reduction in viral replication ($EC_{50}$), the compound concentration reducing cell viability by 50% ($CC_{50}$) and the selectivity index ($SI_{50} : CC_{50}/EC_{50}$) are shown in Table 1.

The antiviral assays were based on inhibition of virus-induced cytopathicity in either 2.2.15 (HBV), HFF (Vaccinia, HCMV), HG23 (NOV), or Vero (Dengue, Measles, Ebola) cell cultures, following previously established procedures (Chen et al, Bio. & Med. Chem. 2014, 22, 6961-6964, including description of assay methods in references 12(a)-(i), which are herein incorporated by reference its its entirety). Confluent cell cultures in 36-well microtitre plates were inoculated with 100 $CCID_{50}$ of virus, 1 $CCID_{50}$ being the virus dose required to infect 50% of the cell cultures. After a 1 hour virus absorption period, residual virus was removed, and the cell cultures were incubated in the presence of varying concentrations of the test compounds. Viral cytopathicity was recorded as soon as it reached completion in the control virus-infected cell cultures that were not treated with the test compounds.

TABLE 1

(Antiviral activity of "D"-Isoneplanocin and "L"-Isoneplanocin (in mM))

| Virus (host cell line) | "D"-Isoneplanocin | "L"-Isoneplanocin |
| --- | --- | --- |
| HBV (2.2.15) | $EC_{50}$ 7.2<br>$EC_{90}$ 35<br>$CC_{50} > 100$<br>$SI_{50} > 14$<br>$SI_{90} > 3$ | inactive |
| Vaccinia (HFF) | $EC_{50}$ 10.08<br>$EC_{90} > 300$<br>$CC_{50} > 300$<br>$SI_{50} > 30$<br>$SI_{90}$ 1 | inactive |

TABLE 1-continued (Antiviral activity of "D"-Isoneplanocin and "L"-Isoneplanocin (in mM))

| Virus (host cell line) | "D"-Isoneplanocin | "L"-Isoneplanocin |
| --- | --- | --- |
| HCMV (HFF) | $EC_{50}$ 0.11<br>$EC_{90} > 12$<br>$CC_{50} > 49.33$<br>$SI_{50} > 448$<br>$SI_{90} < 4$ | $EC_{50}$ 3.70<br>$EC_{90}$ 6.86<br>$CC_{50} > 300$<br>$SI_{50} > 81$<br>$SI_{90} > 44$ |
| NOV (HG23) | $EC_{50}$ 0.784<br>$EC_{90}$ 8.884<br>$CC_{50} > 100$<br>$SI_{50} > 128$<br>$SI_{90} > 11$ | $EC_{50}$ 11<br>$EC_{90}$ 89<br>$CC_{50} > 300$<br>$SI_{50} > 9$<br>$SI_{90} > 1$ |
| Dengue (Vero 76) | $EC_{50}$ 1.1, 1.5<br>$CC_{50}$ 25.3, 23.8<br>$SI_{50}$ 17, 21 | $EC_{50}$ 6.1, 5.7<br>$CC_{50}$ 87, 122<br>$SI_{50}$ 15, 21 |
| Measles (Vero 76) | $EC_{50} < 0.38$<br>$EC_{90}$ ND$^a$<br>$CC_{50} > 1.33$<br>$SI_{50} > 3.5$ | $EC_{50}$ 0.72, 0.72<br>$EC_{90}$ ND$^a$<br>$CC_{50} > 12.2, 15.2$<br>$SI_{50}$ 17, 21 |
| Ebola (Zaire) (Vero) | $EC_{50}$ 0.38<br>$CC_{50}$ 1.3<br>$SI_{50}$ 3.5 | $EC_{50}$ 0.76<br>$CC_{50}$ 11.4<br>$SI_{50}$ 15 |

$^a$ND, not determined

As shown in Table 1, both isoneplanocin enantiomers provide activity towards human cytomegalovirus (HCMV), measles, Ebola, norovirus, and dengue. "D"-Isoneplanocin displayed activity towards hepatitis B virus and vaccinia virus. In general, "D"-Isoneplanocin displayed cytotoxicity at lower concentrations compared to "L"-Isoneplanocin demonstrating a preference for the L-enantiomer as a potential drug candidate for antiviral activity.

Example 4

S-Adenosylhomocysteine Hydrolase (SAHase) Inhibition by "D"-Isoneplanocin and "L"-Isoneplanocin As a consequence of "D"-Isoneplanocin and "L"-Isoneplanocin, being isomers of Neplanocin A, which on one hand is a potent inhibitor of S-adenosylhomocysteine hydrolase (SAHase), a mechanism agreed upon as one source of its antiviral activity and on the other hand thought to contribute to cytotoxicity, the inhibitory efficiency on SAHase activity was assayed (source: rabbit erythrocytes). The inhibition of SAHase activity can be quantitated by the release of free homocysteine. SAHase from rabbit erythrocytes (Sigma) is dialyzed at 4° C. for 2 h in a buffer containing 20% glycerol and 50 mM potassium phosphate pH 7.4. The presence of adenosine deaminase insures that the reaction will proceed in the forward (hydrolysis) direction only. The enzyme preparation is incubated with or without the target compounds at different concentrations in 50 mM potassium phosphate buffer pH 7.4 for 5 minutes at 37° C. before SAH is added. The formation of homocysteine is detected using the Measure-iT™ thiol quantitation reagent according to the manufacturer's instructions (Life technologies, Carlsbad, Calif.). Plates are read on Spectra Max M2 (Molecular Devices).

The assay produced the following results ($IC_{50}$ in nM): Neplanocin A (0.9 nM); "D"-Isoneplanocin A (0.9 nM); "L"-Isoneplanocin A (27 nM). "D"-Isoneplanocin possesses an inhibitory effect on SAHase comparable to Neplanocin A, while a much higher concentration of "L"-Isoneplanocin is required to inhibit SAHase to the same extent, suggesting that the "L"-Isoneoplanicn enantiomer displays a considerably less inhibitory effect on SAHase activity.

Collectively, these data indicated L-Isoneplanocin to be 2 fold less active against Ebola than isomer D- but it was also less toxic. The SAHase inhibitory results suggested a correlation with the Ebola activity for D-Isoneplanocin; however, in the case of L-isoneplanocin the weaker Ebola effect may be due to its reduced impact on the SAHase or the existence of a different anti-Ebola mechanism.

Example 5

Synthesis and Antiviral Properties of 3-Bromo-3-Deazaneplanocin and 3-Bromo-3-Deazaaristeromycin In order to explore antiviral mechanisms initiated by 3-deazaadenine carbocyclic nucleosides, 3-bromo-3-deazaneplanocin and 3-bromo-3-deazaaristeromycin can be synthesized from a readily available cyclopentenol and cyclopentanone and either 4-amino- or 4-chloro-1H-imidazo [4,5-c]pyridine (6-amino- or 6-chloro-3-deazaadenine) in 5 steps and 7 steps, as described in Liu et al 2012.

The antiviral properties of 3-Bromo-3-deazaneplanocin and 3-Bromo-3-deazaaristeromycin, analogues of 3-Deazaneplanocin, are assayed such as prior example 3. Both compounds were evaluated against both DNA and RNA viruses and Tables 2 and 3 list where activity was observed. Moreover, activity against a panel of influenza viruses is shown in Table 4.

TABLE 2

(Antiviral activity of 3-Bromo-3-deazaneplanocin)

| Virus | Cell line | $EC_{50}$[a] mM | $CC_{50}$[b] mM | $CC_{50}/EC_{50}$ |
|---|---|---|---|---|
| Marburg | HeLa | 0.009 | 10 | 1100 |
| Ebola | HeLa | 3.3 | 11 | 3 |

[a]Compound concentration that reduces viral replication by 50%
[b]Compound concentration that reduces cell viability by 50%

TABLE 3

(Antiviral activity of 3-Bromo-3-deazaneplanocin and 3-Bromo-3-deazaaristeromycin)

| | | 3-Bromo-3-deazaneplanocin | | | 3-Bromo-3-deazaaristeromycin | | |
|---|---|---|---|---|---|---|---|
| Virus | Cell line | $EC_{50}$[a] | $CC_{50}$[b] MCC[d] | SI[c] | $EC_{50}$[a] | $CC_{50}$[b] | SI[c] |
| Rift Valley Fever | Vero 76 | <0.094 | 23.2[b] | 250 | 58.3 | >290 | 5 |
| Punta Toro | Vero 76 | 0.25 | 35[b] | 140 | | | |
| Tacaribe | Vero 76 | <0.094 | 188[b] | >2000 | 9.9 | 79 | 7.9 |
| Pichinde | Vero | 1.2 | 27.5[b] | 24 | | | |
| Junin | Vero | 0.094 | 15.2[b] | 160 | 93 | | |
| Dengue | Vero | 2.9 | 167[b] | 57 | 230 | 184 | 2 |
| Vaccinia | HeLa | 0.5 | >100[d] | | | >300 | >1.3 |
| Vesicular stomatitis | HeLa | 0.4 | 100[d] | | | | |
| Epstein Barr | Akata | >0.03 | 0.13[b] | <4.3 | | | |
| Parainfluenza-3 | Vero | 0.5 | >100[d] | | | | |
| Feline herpes | CRFK | 0.2 | 94[b] | 470 | | | |

[a]$EC_{50}$ compound concentration that reduces viral replication by 50%
[b]$CC_{50}$ compound concentration that reduces cell viability by 50%
[c]$SI_{50}$: $CC_{50}/EC_{50}$
[d]MCC: minimum compound concentration that causes a microscopically detectable alternation of normal cell morphology

TABLE 4

(In vitro activities of 3-Bromo-3-deazaneplanocin and 3-Bromo-3-deazaaristeromycin against influenza viruses (in mM)[abc])

| | | 3-Bromo-3-deazaneplanocin | | | 3-Bromo-3-deazaaristeromycin | | |
|---|---|---|---|---|---|---|---|
| Virus | Cell line | [a]$EC_{50}$ | [b]$CC_{50}$ | [c]SI | [a]$EC_{50}$ | [b]$CC_{50}$ | [c]SI |
| Flu A (H1N1) | MDCK | <0.094 | 220 | >2345 | >290 | >290 | 0 |
| Flu A (H3N2) | MDCK | 1.55 | >290 | >190 | >290 | >290 | 0 |
| Flu A (H5N1) | MDCK | 0.94 | >290 | >310 | 1.14 | >290 | >260 |
| Influenza B | MDCK | >0.16 | 1.1 | <7 | 0.84 | >290 | >340 |

[a]$EC_{50}$ compound concentration that reduces viral replication by 50%
[b]$CC_{50}$ compound .concentration that reduces cell viability by 50%
[c]SI: $CC_{50}/EC_{50}$ Antiviral analysis found 3-Bromo-3-deazaneplanocin to display significant activity towards a number of (−)-ssRNA and a few dsDNA viruses. 3-Bromo-3-deazaaristeromycin was less active than 3-Bromo-3-deazaneplanocin against selected examples of those viruses affected by 3-Bromo-3-deazaneplanocin. 3-Bromo-3-deazaneplanocin shows a greater efficiency at reducing viral replication, albeit with increased cytotoxicity compared to 3-Bromo-3-deazaaristeromycin as shown in Tables 3 & 4. Importantly, 3-Bromo-3-deazaneplanocin displays antiviral activity to a large panel of DNA and RNA viruses, suggesting its utility as a broad spectrum viral hemorrhagic fever agent.

Example 6

S-Adenosylhomocysteine Hydrolase (SAHase) Inhibition by 3-Deazaneplanocin and 3-Bromo-3-Deazaneplanocin 3-Deazaneplanocin and 3-Bromo-3-deazaneplanocin were evaluated against the inhibitory efficiency of SAHase (depicted in FIG. 6 as SAHase activity quantitated by release of free homocysteine), such as described in prior example 4. The results are shown in Table 5 and FIG. 7.

TABLE 5

(Inhibitory properties versus SAHase ($IC_{50}$)[a])

| Compound | $IC_{50}$ |
|---|---|
| 3-Deazaneplanocin | 9.3 nM |
| "D"-Isoneplanocin | 0.9 nM |
| "L"-Isoneplanocin | 27 nM |
| "D"-3-Deazaisoneplanocin | 3.19 nM |
| "L"-3-Deazaisoneplanocin | >10,000 nM |
| 3-Bromo-3-deazaneplanocin | 2.7 nM |

[a]From rabbit erythrocytes

This assay produced the following results ($IC_{50}$ in nM): 3-Deazaneplanocin (9.3 nM); 3-Bromo-3-Deazaneplanocin (2.7 nM) (Table 5). 3-Bromo-3-Deazaneplanocin shows less efficiency at inhibiting SAHase when compared to 3-deazaneplanocin (as shown in Table 5), as shown in FIG. 7. The chemical structures of the evalulated neplanocin analogues are shown in FIG. 8 (D-3-deazaisoneplanocin (FIG. 8A), L-3-deazaisoneplanocin (FIG. 8B), D-3-bromo-3-deazaneplanocin (FIG. 8C) and L-3-bromo-3-deazaneplanocin (FIG. 8D). The broad antiviral activity seen with 3-Bromo-3-Deazaneplanocin correlates with inhibition of SAHase, suggesting that targeting of this cellular enzyme largely provides the mechanism of 3-Bromo-3-Deazaneplanocin antiviral activity. Development of therapeutics that target host-encoded functions, such as 3-Bromo-3-Deazaneplanocin, is advantageous not only to reduce resistance development but also to increase potential for broad-spectrum antiviral activity.

Example 7

Synthesis and Antiviral Activity of
"D"-3-Deazaisoneplanocin and
"L"-3-Deazisoneplanocin The previous studies with neplanocin-based (examples 3 and 5) antiviral candidates led to evaluation of isomeric 1',6'-iso-3-deazaneplanocin which based on earlier analysis of its dramatic structural differences is evaluated for its distinct antiviral properties. The analysis was concurrent with interest in L-like carbocyclic nucleoside series, which had received little attention as a source of antiviral candidates but was an attractive structural feature because of the decreased toxicity associated with the L-ribofuranosyl nucleosides. Thus, these interests were combined to seek "D-" and "L-"1',6'-iso-3-deazaneplanocin and analogs therefrom as antiviral candidates. The synthesis of "D"-3-Deazaisoneplanocin and "L"-3-Deazaisoneplanocin in a scheme such as prior examples 1, 2, and 5.

Antiviral tests were conducted on "D"-3-Deazaisoneplanocin and "L"-3-Deazaisoneplanocin using the following assays: measles virus (visual) and (neutral red), human cytomegalovirus (crystal violet), and Ebola virus (Real Time Polymerase Chain Reaction). The antiviral activity of the compounds were tested in vitro in Vero 76 cell line for measles, HFF cell line for HCMV and HepG cell line for Ebola.

"D"-3-Deazaisoneplanocin and "L"-3-Deazaisoneplanocin data: measles: "D"-3-Deazaisoneplanocin, $EC_{50}<0.1$, $CC_{50}>100$, $SI_{50}>1000$; drug assay: visual (cytopathic effect/toxicity). Measles: "D"-3-Deazaisoneplanocin, $EC_{50}<0.1$, $CC_{50}$ 43, $SI_{50}>430$; drug assay: neutral red (cytopathic effect/toxicity). measles: "L"-3-Deazaisoneplanocin, $EC_{50}$ 8.7, $CC_{50}>100$, $SI_{50}>11$; drug assay: visual (cytopathic effect/toxicity). Measles: "L"-3-Deazaisoneplanocin, $EC_{50}$ 5.5, $CC_{50}>100$, $SI_{50}$ 18; drug assay: neutral red (cytopathic effect/toxicity). HCMV: "D"-3-Deazaisoneplanocin, $EC_{50}<0.1$, $CC_{50}>300.00$, $SI_{50}>3000$, $EC_{90}<0.10$, $SI_{90}>3000$; drug assay: crystal violet (cytopathic effect/toxicity). HCMV: "L"-3-Deazaisoneplanocin, $EC_{50}<0.1$, $CC_{50}>300.00$, $SI_{50}>3000$, $EC_{90}<0.10$, $SI_{90}>3000$; drug assay: crystal violet (cytopathic effect/toxicity). Ebola: "D"-3-Deazaisoneplanocin, $EC_{50}<0.32$; $CC_{50}>100.00$, $SI_{50}>313$, $EC_{90}>74.10$, $SI_{90}>1$; drug assay: real time polymerase chain reaction (virus yield reduction/CellTiter 96, toxicity). Ebola: "L"-3-Deazaisoneplanocin, $EC_{50}<03.2$; $CC_{50}>100.00$, $SI_{50}>312$, $EC_{90}<0.32$, $SI_{90}>312$; drug assay: real time polymerase chain reaction (virus yield reduction/CellTiter 96, toxicity).

TABLE 6

(Antiviral properties of "D-" and "L-" 3-Deazaisoneplanocin)

| | | "D"-3-Deazaisoneplanocin | | | | "L"-3-Deazaisoneplanocin | | | |
|---|---|---|---|---|---|---|---|---|---|
| Virus | Cell line | $EC_{50}$ | $EC_{90}$ | $CC_{50}$ | $SI_{50}$ | $EC_{50}$ | $EC_{90}$ | $CC_{50}$ | $SI_{50}$ |
| Measles Virus | Vero 76 | <0.1 | | >100 | >1000 | 8.7 | | >100 | >11 |
| Human cytomegalovirus | HFF | <0.10 | <0.10 | >300 | >3000 | <0.10 | <0.10 | >300 | >3000 |
| Ebola (Zaire) | HepG | <0.32 | 74.1 | >100.00 | >313 | <0.32 | <0.32 | >100.00 | >312 |

$EC_{50}$ Compound concentration that reduces viral replication by 50%
$EC_{90}$ Compound concentration that reduces viral replication by 90%
$CC_{50}$ Compound concentration that reduces cell viability by 50%
$SI_{50}$ $CC_{50}/EC_{50}$ D- and L-3-deazaisonepalnocin enantiomers display activity against Measles virus (Vero 76), Human cytomegalovirus (HFF) and Ebola (HepG). The $IC_{50}$ Ebola (Zaire) data in HepG cells showed both enantiomers to be equipotent and non-cytotoxic ($IC_{50}<0.32$ mM; $CC_{50}>100$ mM) yet at $IC_{90}$ "L"-3-Deazaisoneplanocin was more potent ($IC_{90}<0.32$ mM compared to "D"-3-Deazaisoneplanocin, $IC_{90}$ 74.1 mM). Equally relevant was the SAHase data for the two enantiomers (Table 5 and example 8); D-5 ($IC_{50}$ 3.19 nM) and "L"-3-Deazaisoneplanocin ($IC_{50}>10,000$ nM). Collectively, this data suggests that the Ebola results for "D"-3-deazaisoneplanocin correlate with its SAHase effect but the same is not true for "L"-3-deazaisoneplanocin. Interestingly, two anti-Ebola candidates have been identified that are enantiomers but are acting by different mechanisms. This anti-Ebola efficacy is further shown in Table 7.

TABLE 7

| Compound | Cell line | $^aEC_{50}$ | $^bCC_{50}$ | $CC_{50}/EC_{50}$ |
|---|---|---|---|---|
| "D"-3-Deazaisoneplanocin | HepG | <0.32 mM | >100 mM | >313 mM |
| "L"-3-Deazaisoneplanocin | HepG | <0.32 mM | >100 mM | >313 mM |

[a]Compound concentration that reduces viral replication by 50%
[b]Compound concentration that reduces cell viability by 50%

Example 8

The antiviral tests were conducted along side control compounds for Measles virus, Human Cytomegalovirus, and Ebola virus. The following control assays were applied: measles virus (visual) and (neutral red), human cytomegalovirus (crystal violet), and Ebola virus (Real Time Polymerase Chain Reaction). The antiviral activity of the control compounds were tested in vitro in Vero 76 cell line for measles, HFF cell line for HCMV and HepG cell line for Ebola.

Control drug reference data: Measles: 3-Deazaguanine, $EC_{50}$ 3.2; $CC_{50}$>100, $SI_{50}$>31; control assay: visual (cytopathic effect/toxicity). Measles: 3-Deazaguanine, $EC_{50}$ 2.1; $CC_{50}$>100, $SI_{50}$>48; control assay: neutral red (cytopathic effect/toxicity). HCMV: ganciclovir, $EC_{50}$ 0.47; $CC_{50}$>300, $SI_{50}$>638, $EC_{90}$ 0.92, $SI_{90}$>326; control assay: crystal violet (cytopathic effect/toxicity). Ebola: carbocyclic 3-deazaadenosine (1), $EC_{50}$ <1.26; $CC_{50}$>126.50, $SI_{50}$>100, $EC_{90}$>126.50, $SI_{90}$ 1; control assay: real time polymerase chain reaction (virus yield reduction/CellTiter 96, toxicity). Ebola: carbocyclic 3-deazaadenosine (2), $EC_{50}$ 7.69; $CC_{50}$>400.00, $SI_{50}$>52; control assay: control assay: real time polymerase chain reaction (virus yield reduction/CellTiter 96, toxicity). Ebola: E-64D, $EC_{50}$ 8.44, $CC_{50}$>400.00 $SI_{50}$>47, $EC_{90}$ 65.40, $SI_{90}$>6; control assay: real time polymerase chain reaction (virus yield reduction/CellTiter 96, toxicity).

Interestingly, "D"-3-Deazaisoneplanocin (<0.1 mg/ml) displayed high antiviral properties towards measles, requiring approximately 20 to 30 times lower drug concentration to reduce viral replication to the same extent as the control drug, 3-Deazaguanine (3.2 mg/ml; 2.1 mg/ml), while maintaining similar levels of cytotoxicity. The "L-" enantiomer was found to be moderately active towards measles, likewise between 55 to 87 times higher drug concentration (5.5 mg/ml; 8.7 mg/ml) are required to obtain similar inhibition of viral replication by the "D-" enantiomer.

Furthermore, both "D-"-Deazaisoneplanocin and "L"-3-deazaisonepalnocin were shown to be highly active toward HCMV. Compared with the control drug, Ganciclovir, both "D-" and "L"-Deazaisoneplanocin require 4 and 9 times less drug concentration to reduce viral replication by 50% and 90% respectively. Importantly, the antiviral properties were not accompanied with increased cytotoxicity compared to Ganciclovir in this assay.

Lastly, "D-" and "L"-3-Deazaisoneplanocin were both shown to be highly active towards Ebola, requiring approximately 3.9 to 26 times lower drug concentrations to reduce Ebola replication by 50% compared to control compounds, Carbocyclic 3-deazaadenosine and E-64D. Treatment of HepG2 cells with <0.32 mM "L"-3-Deazaisoneplanocin inhibited viral replication by 90% whereas between approximately 395 to 750 times higher drug concentration for Carbocyclic 3-deazaadenosine (>126.5 mM; 240.3 mM), 200 times higher drug concentration for E-64D (65.4 mM) and 230 times higher drug concentration for "D"-3-deazaisoneplanocin (74.1 mM) are required to reduce Ebola replication to the same extent. However, the increase in anti-Ebola activity observed with "D-" and "L"-deazaisoneplanocin are also accompanied by an increase in cytotoxicity compared to the controls compounds.

Example 9

S-Adenosylhomocysteine Hydrolase (SAHase) Inhibition by "D"-3-Deazaisoneplanocin and "L"-3-Deazaisoneplanocin This assay produced the following results ($IC_{50}$ in nM): "D"-3-Deazaisoneplanocin (3.19 nM), and "L"-3-Deazaisoneplanocin (>10,000 nM) (as shown above in Table 5). "L"-3-Deazaisoneplanocin displays significantly less of an inhibitory effect on SAHase compared to any other compound tested in Table 5. The potent effect of "L"-3-Deazaisoneplanocin versus Ebola coupled with its weaker properties towards SAHase suggests that SAHase inhibition is not the only site where "L"-3-Deazaisoneplanocin is acting towards this virus.

The inventions being thus described provides a description of the manufacture and use of the disclosed compositions and methods, it will be obvious that the same may be varied in many ways. Such variations are not to be regarded as a departure from the spirit and scope of the inventions and all such modifications are intended to be included within the scope of the following claims.

What is claimed is:

1. A neplanocin compound of one of the following formulae:

L-isoneplanocin analogue,

D-3-Deazaisoneplanocin analogue,

L-3-Deazaisoneplanocin analogue, a pharmaceutically-acceptable prodrug precursor thereof, or salt thereof;

Wherein

R is a hydrogen or a hydroxyl group, halogen, or $C_1$-$C_4$ alkyl optionally substituted with a hydroxyl group, R2' is a hydrogen or a hydroxyl group, halogen, or $C_1$-$C_4$ alkyl optionally substituted with a hydroxyl group, R3' is a hydrogen or a hydroxyl group, halogen, or $C_1$-$C_4$ alkyl optionally substituted with a hydroxyl group, R6' is a hydrogen or halogen, W is a hydrogen or a halogen, X is $NH_2$, NHR", NR'R", NHOH, or hydrogen (wherein the R' and R" independently are alkyl, aryl or arylalkyl), Y is a hydrogen, a hydroxyl group, $CH_2OH$, $CH_2NH_2NHR'$, NR'R" (wherein the R" and R' are alkyl, aryl or arylalkyl), $CH_2X$ (wherein X is a halogen), or a $C_1$-$C_4$ alkyl optionally substituted with a hydroxyl group, Y' is a hydrogen, $CH_2OH$, $CH_2NH_2$, NRR', NHR" (wherein the R" and R' are independently alkyl, aryl or arylalkyl), $CH_2X$ (wherein X is a halogen), or a $C_1$-$C_4$ alkyl optionally substituted with a hydroxyl group, and Z is a hydrogen, halogen, alkyl or substituted alkyl, or cyano.

2. The neplanocin compound of claim 1, wherein the formula is the following:

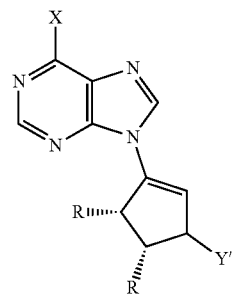

L-isoneplanocin analogue, or a pharmaceutically-acceptable prodrug precursor thereof, or salt thereof, Wherein R is a hydrogen or a hydroxyl group, Y' is a hydrogen, $CH_2OH$, and X is $NH_2$ or hydrogen.

3. The neplanocin compound of claim 1, wherein the formula is one of the following:

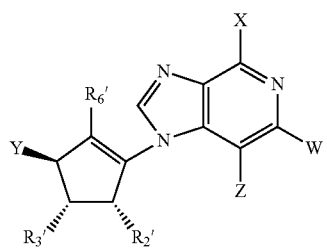

D-3-Deazaisoneplanocin analogue,

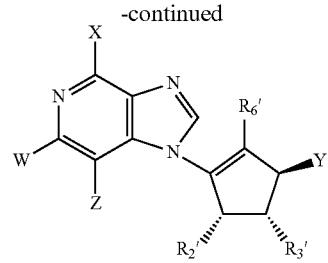

L-3-Deazaisoneplanocin analogue, or a pharmaceutically-acceptable prodrug precursor thereof, or salt thereof, Wherein R2' is a hydrogen, hydroxyl group, or halogen, R3' is a hydrogen, hydroxyl group, or halogen, R6' is a hydrogen or halogen, W is a hydrogen or a halogen, X is $NH_2$ or hydrogen, Y is a hydrogen, hydroxyl group, $CH_2X$ (wherein X is a halogen), or $C_1$-$C_4$ alkyl group optionally substituted with a hydroxyl group, and Z is a hydrogen, halogen, or alkyl group.

4. The neplanocin compound of claim 3, wherein the formula is one of the following:

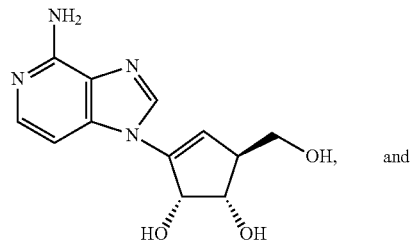

L-3-deazaisoneplanocin

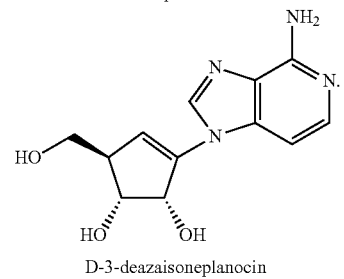

D-3-deazaisoneplanocin

5. The neplanocin compound of claim 3, wherein Z is a halogen.

6. The neplanocin compound of claim 5, wherein the formula is one of the following:

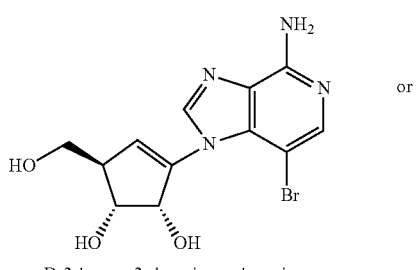

D-3-bromo-3-deazaisoneplanocin

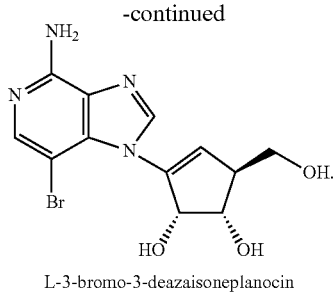

L-3-bromo-3-deazaisoneplanocin

7. A neplanocin compound of one of the following formulae:

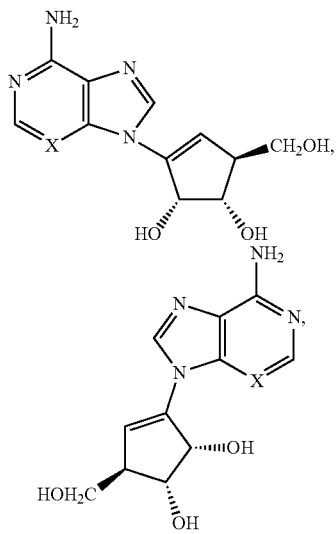

a pharmaceutically-acceptable prodrug precursor or salt thereof, wherein X is N, CH, or C (halogen).

8. The neplanocin compound of claim 7, wherein X is CBr.

9. A pharmaceutical composition for treating a subject with a viral infection or in need of prophylactic antiviral treatment comprising: an antiviral sufficient amount of the neplanocin compound of claim 1 to produce antiviral effects and a pharmaceutically acceptable carrier selected from the group consisting of a diluent, adjuvant, excipient, and vehicle.

10. The pharmaceutical composition of claim 9, wherein the pharmaceutical composition is formulated into tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols.

11. The pharmaceutical composition of claim 9, wherein the antiviral amount of neplanocin compound is an amount sufficient to improve, inhibit, prevent or ameliorate the viral infection.

12. The pharmaceutical composition of claim 9, wherein the antiviral effective amount is an amount that prevents the occurrence or one or more symptoms of the infection or reduces the severity of, or the length of time during which the subject suffers from, one or more symptoms of the infection by at least 50%.

13. The pharmaceutical composition of claim 9, wherein the antiviral effective amount is an amount that reduces viral replication or kills viral cells by at least 50%.

14. A method of therapeutic treatment of a subject against viral infection comprising: administering a therapeutically effective amount of at least one neplanocin compound of claim 1 to a subject in need of antiviral therapeutic treatment.

15. The method of claim 14, wherein the administering is by ingestion, injection, infusion, or other bodily administration.

16. The method of claim 14, wherein the virus is a DNA virus.

17. The method of claim 14, wherein the virus is a RNA virus.

18. The method of claim 14, wherein the virus is selected from the group consisting of Arenaviridae, Bunyaviridae, Coronaviridae, Flexiviridae, Hepevirus, Orthomyxoviridae, Paramyxoviridae, Picornaviridae, Togaviridae, Herpesviridae, Papovaviridae, Poxviridae, hepatic viruses, and norovirus.

19. The method of claim 18, wherein the virus is human cytomegalovirus (HCMV), measles, Ebola, norovirus (NOV), dengue, vaccinia or hepatitis B virus (HBV).

20. The method of claim 14, wherein the virus is Ebola and the neplanocin compound is carbocyclic nucleoside having at least one of the formulae:

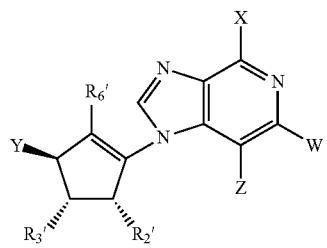

D-3-Deazaisoneplanocin analogue,

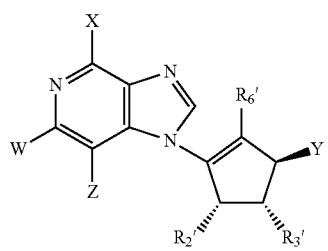

L-3-Deazaisoneplanocin analogue, a pharmaceutically-acceptable prodrug precursor thereof, or salt thereof, Wherein
R2' is a hydrogen, hydroxyl group, or halogen,
R3' is a hydrogen, hydroxyl group, or halogen,
R6' is a hydrogen or halogen,
W is a hydrogen or a halogen,
X is NH₂ or hydrogen,
Y is a hydrogen or a hydroxyl group, and
Z is a hydrogen, halogen, or alkyl group.

21. The method of claim 14, wherein the virus is Ebola and the neplanocin compound has at least one of the following formulae:

L-3-deazaisoneplanocin or

D-3-deazaisoneplanocin

22. The method of claim 14, wherein the amount of neplanocin compound administered is an antiviral effective amount sufficient to improve, inhibit, prevent or ameliorate the viral infection.

23. The method of claim 22, wherein the antiviral effective amount is an amount that prevents the occurrence or one or more symptoms of the infection or reduces the severity of, or the length of time during which the subject suffers from, one or more symptoms of the infection by at least 50%.

24. The method of claim 14, wherein the enantiomer neplanocin compound are provided for dual mechanisms of antiviral efficacy.

* * * * *